(12) United States Patent
Miller et al.

(10) Patent No.: US 7,598,290 B2
(45) Date of Patent: Oct. 6, 2009

(54) CYTOTOXIC AGENTS COMPRISING NEW C-2 MODIFIED TAXANES

(75) Inventors: Michael L. Miller, Framingham, MA (US); Ravi V. J. Chari, Newton, MA (US); Erkan Baloglu, Stoneham, MA (US)

(73) Assignee: Immunogen, Inc., Waltham, MA (US)

( * ) Notice: Subject to any disclaimer, the term of this patent is extended or adjusted under 35 U.S.C. 154(b) by 0 days.

(21) Appl. No.: 11/679,347

(22) Filed: Feb. 27, 2007

(65) Prior Publication Data

US 2007/0270482 A1 Nov. 22, 2007

Related U.S. Application Data

(63) Continuation of application No. 11/464,718, filed on Aug. 15, 2006, now abandoned, which is a continuation of application No. 11/294,311, filed on Dec. 5, 2005, now abandoned.

(51) Int. Cl.
*A61K 31/335* (2006.01)
*C07D 305/00* (2006.01)
(52) U.S. Cl. ...................... 514/449; 549/510
(58) Field of Classification Search .............. 549/570; 574/449
See application file for complete search history.

(56) References Cited

U.S. PATENT DOCUMENTS

| 6,589,979 B2 * | 7/2003 | Bombardelli et al. | ....... 514/449 |
| 7,186,851 B2 * | 3/2007 | Baloglu | ....... 549/510 |

FOREIGN PATENT DOCUMENTS

| EP | 0617034 | * | 9/1994 |
| EP | 0617034 A | | 9/1994 |
| WO | 0138318 A | | 5/2001 |
| WO | 200138318 A | | 5/2001 |
| WO | 03097625 A | | 11/2003 |
| WO | 2003097625 A | | 11/2003 |
| WO | 2004013093 A | | 2/2004 |

OTHER PUBLICATIONS

K. C. Nicolaou et al., "Chemical synthesis and biological evaluation of c-2 taxoids", Journal of the American Chemical Society, vol. 117, No. 9, pp. 2409-2420, 1995.
Kim et al., "C-2 modified taxol Analogs with Improved Aqueous Solubility", Bull. Korean Chem. Soc., vol. 20, No. 12, pp. 1389-1390, 1999.
Ojima Iwao, et al., "Tumor-specific novel taxoid-monoclonal antibody conjugates", Journal of Medicinal Chemistry, vol. 45, No. 26, pp. 5620-5623, Dec. 19, 2002.
M. L. Miller, et al., "Synthesis of potent taxoids for tumor-specific delivery using monoclonal antibodies", Bioorganic & Medicinal Chemistry Letters, vol. 14, No. 15, pp. 4079-4082, Aug. 2, 2004.
M. L. Miller, et al., "Synthesis of taxoids with improved cytotoxicity and solubility for use in tumor-specific delivery", Journal of Medicinal Chemistry, vol. 47, No. 20, pp. 4802-4805, Sep. 23, 2004.
K. C. Nicolaou et al., "Chemical synthesis and biological evaluation of c-2 taxoids", Journal of the American Chemical Society, vol. 117, No. 9, pp. 2409-2420, 1995.
Kim et al., "C-2 modified taxol Analogs with Improved Aqueous Solubility", Bull. Korean Chem. Soc., vol. 20, No. 12, pp. 1389-1390, 1999.
Ojima Iwao, et al., "Tumor-specific novel taxoid-monoclonal antibody conjugates", Journal of Medicinal Chemistry, vol. 45, No. 26, pp. 5620-5623, Dec. 19, 2002.
M. L. Miller, et al., "Synthesis of potent taxoids for tumor-specific delivery using monoclonal antibodies", Bioorganic & Medicinal Chemistry Letters, vol. 14, No. 15, pp. 4079-4082, Aug. 2, 2004.
M. L. Miller, et al., "Synthesis of taxoids with improved cytotoxicity and solubility for use in tumor-specific delivery", Journal of Medicinal Chemistry, vol. 47, No. 20, pp. 4802-4805, Sep. 23, 2004.

* cited by examiner

*Primary Examiner*—Janet L. Andres
*Assistant Examiner*—Raymond Covington
(74) *Attorney, Agent, or Firm*—Sughrue Mion, PLLC

(57) ABSTRACT

The invention relates to taxanes and to novel cytotoxic agents comprising taxanes and their therapeutic use as a result of delivering the taxanes to a specific cell population in a targeted fashion by chemically linking the taxane to a cell binding agent.

45 Claims, 2 Drawing Sheets

Fig. 1 Relative binding affinities of huC242 antibody and its taxoid conjugate huC242-IGT-16-141
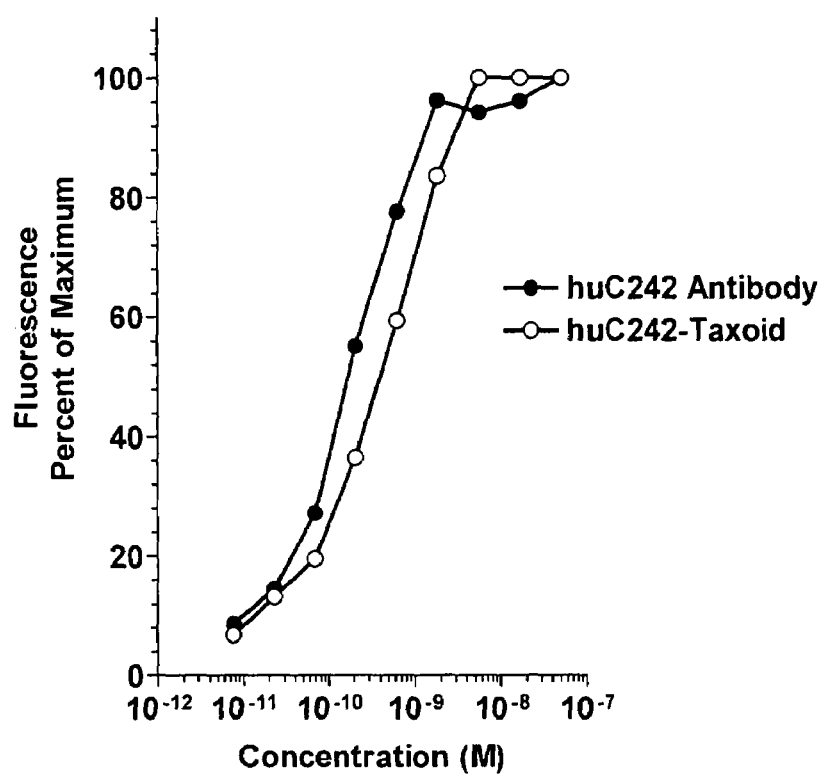

Fig. 2a In vitro potency of huC242-Taxoid IGT-16-141 towards antigen positive COLO 205 cells and antigen negative A-375 cells.
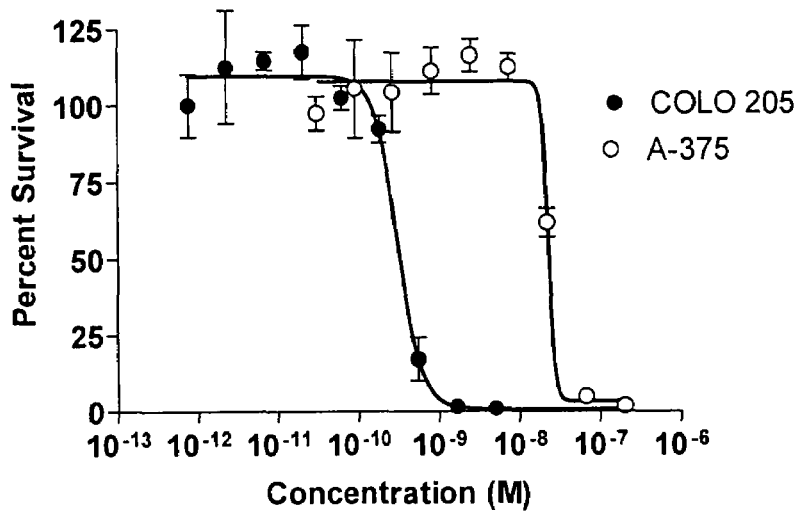
Fig. 2b In vitro potency of free Taxoid IGT-16-141 towards COLO 205 and A-375 cells.
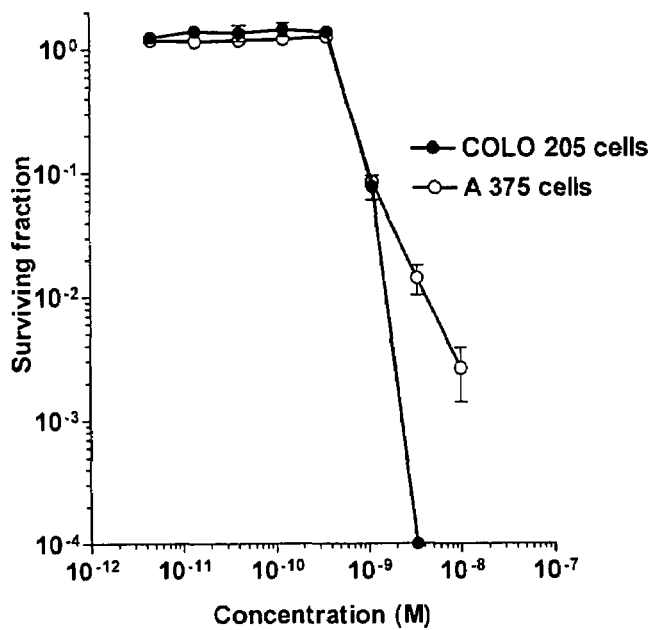

CYTOTOXIC AGENTS COMPRISING NEW C-2 MODIFIED TAXANES

This is a continuation of application Ser. No. 11/464,718 filed Aug. 15, 2006 (abandoned), which is a continuation of application Ser. No. 11/294,311 filed Dec. 5, 2005 (abandoned).

FIELD OF THE INVENTION

The present invention relates to novel cytotoxic agents and their therapeutic use. More specifically, the invention relates to novel cytotoxic agents comprising taxanes and their therapeutic use. These novel cytotoxic agents have therapeutic use as a result of delivering the taxanes to a specific cell population in a targeted fashion by chemically linking the taxane to a cell binding agent.

BACKGROUND OF THE INVENTION

Many reports have appeared on the attempted specific targeting of tumor cells with monoclonal antibody-drug conjugates (Sela et al, in *Immunoconjugates* 189-216 (C. Vogel, ed. 1987); Ghose et al, in *Targeted Drugs* 1-22 (E. Goldberg, ed. 1983); Diener et al, in *Antibody mediated delivery systems* 1-23 (J. Rodwell, ed. 1988); Pietersz et al, in *Antibody mediated delivery systems* 25-53 (J. Rodwell, ed. 1988); Bumol et al, in *Antibody mediated delivery systems* 55-79 (J. Rodwell, ed. 1988). All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46 *Cancer Res.* 2407-2412 (1986); Ohkawa et al 23 *Cancer Immunol. Immunother.* 81-86 (1986); Endo et al, 47 *Cancer Res.* 1076-1080 (1980)), dextran (Hurwitz et al, 2 *Appl. Biochem.* 25-35 (1980); Manabi et al, 34 *Biochem. Pharmacol.* 289-291 (1985); Dillman et al, 46 *Cancer Res.* 4886-4891 (1986); Shoval et al, 85 *Proc. Natl. Acad. Sci.* 8276-8280 (1988)), or polyglutamic acid (Tsukada et al, 73 *J. Natl. Canc. Inst.* 721-729 (1984); Kato et al 27 *J. Med. Chem.* 1602-1607 (1984); Tsukada et al, 52 *Br. J. Cancer* 111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048-1054 (1981)). Yang and Reisfeld used the same technique to conjugate daunorubicin to an anti-melanoma antibody (80 *J. Natl. Canc. Inst.* 1154-1159 (1988)). Dillman et al. also used an acid-labile linker in a similar fashion to prepare conjugates of daunorubicin with an anti-T cell antibody (48 *Cancer Res.* 6097-6102 (1988)).

An alternative approach, explored by Trouet et al, involved linking daunorubicin to an antibody via a peptide spacer arm (79 *Proc. Natl. Acad. Sci.* 626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035-12041 (1985); Lambert et al, in *Immunotoxins* 175-209 (A. Frankel, ed. 1988); Ghetie et al 48 *Cancer Res.* 2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al (260 *J. Biol. Chem.* 10905-10908 (1985)) described the conversion of methotrexate into a mercaptoethylamide derivative followed by conjugation with poly-D-lysine via a disulfide bond. Another report described the preparation of a conjugate of the trisulfide containing toxic drug calicheamycin with an antibody (Hinman et al., 53 *Cancer Res.* 3336-3342 (1993)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream.

In spite of the above described difficulties, useful cytotoxic agents comprising cell binding moieties and the group of cytotoxic drugs known as maytansinoids have been reported (U.S. Pat. Nos. 5,208,020, 5,416,064, and R. V. J. Chari, 31 *Advanced Drug Delivery Reviews* 89-104 (1998)). Similarly, useful cytotoxic agents comprising cell binding moieties and analogues and derivatives of the potent antitumor antibiotic CC-1065 have also been reported (U.S. Pat. Nos. 5,475,092 and 5,585,499).

Paclitaxel (Taxol), a cytotoxic natural product, and docetaxel (Taxotere), a semi-synthetic derivative, are widely used in the treatment of cancer. These compounds belong to the family of compounds called taxanes. Taxanes are mitotic spindle poisons that inhibit the depolymerization of tubulin, resulting in an increase in the rate of microtubule assembly and cell death. While docetaxel and paclitaxel are useful agents in the treatment of cancer, their antitumor activity is limited because of their non-specific toxicity towards normal cells.

Further, compounds like paclitaxel and docetaxel themselves are not sufficiently potent to be used in conjugates of cell binding agents. Recently, a few new docetaxel analogs with greater potency than either docetaxel or paclitaxel have been described (Iwao Ojima et al., *J. Med. Chem.* 39, 3889-3896 (1996). However, these compounds lack a suitable functionality that allows linkage via a cleavable bond to cell binding agents.

Accordingly, a method of treating diseases with taxanes wherein their side effects are reduced without compromising their cytotoxicity is greatly needed.

U.S. Pat. Nos. 6,436,931, 6,372,738 and 6,340,701 described taxanes linked by a disulfide bridge to the monoclonal antibody. Those taxanes seem to be not sufficiently potent to be used.

SUMMARY OF THE INVENTION

As disclosed in a first embodiment, one object of the present invention is to provide taxanes that are highly toxic and that can still be effectively used in the treatment of many diseases.

Another object of the present invention is to provide novel taxanes.

In a second embodiment, the present invention provides a cytotoxic agent comprising one or more taxanes linked to a cell binding agent.

In a third embodiment the present invention provides a therapeutic composition comprising:
(A) an effective amount of one or more taxanes linked to a cell binding agent, and
(B) a pharmaceutically acceptable carrier, diluent, or excipient In a fourth embodiment, the present invention provides a method of killing selected cell populations comprising contacting target cells or tissue containing target cells, with a cytotoxic amount of a cytotoxic agent comprising one or more taxanes linked to a cell binding agent.

BRIEF DESCRIPTION OF THE DRAWINGS

FIG. 1 is a graph showing the relative binding affinities of huC242 antibody and its taxoid conjugate huC242-IGT-16-141.

FIG. 2a is a graph showing the in vitro potency of huC242-taxoid IGT-16-141 towards antigen positive COLO 205 cells and antigen negative A-375 cells.

FIG. 2b is a graph showing the in vitro potency of free taxoid IGT-16-141 towards COLO-205 and -375 cells.

DETAILED DESCRIPTION OF THE INVENTION

This invention is based on the synthesis of novel taxanes that retain high cytotoxicity and that can be effectively linked to cell binding agents. It has previously been shown that the linkage of highly cytotoxic drugs to antibodies using a cleavable link, such as a disulfide bond, ensures the release of fully active drug inside the cell, and such conjugates are cytotoxic in an antigen specific manner (U.S. Pat. Nos. 6,340,701; 6,372,738; 6,436,931). However, the art reveals that it is extremely difficult to modify existing drugs without diminishing their cytotoxic potential. The disclosed invention overcomes this problem by modifying the disclosed taxanes with chemical moieties. As a result, the disclosed novel taxanes preserve, and in some cases could even enhance, the cytotoxic potency of known taxanes. The cell binding agent-taxane complexes permit the full measure of the cytotoxic action of the taxanes to be applied in a targeted fashion against unwanted cells only, therefore, avoiding side effects due to damage to non-targeted healthy cells. Thus, the invention provides useful agents for the elimination of diseased or abnormal cells that are to be killed or lysed such as tumor cells (particularly solid tumor cells).

The cytotoxic agent according to the present invention comprises one or more taxanes linked to a cell binding agent via a linking group. The linking group is part of a chemical moiety that is covalently bound to a taxane through conventional methods. In a preferred embodiment, the chemical moiety can be covalently bound to the taxane via an ester, ether or carbamate linkage.

The taxanes useful in the present invention have the formula (I) shown below:

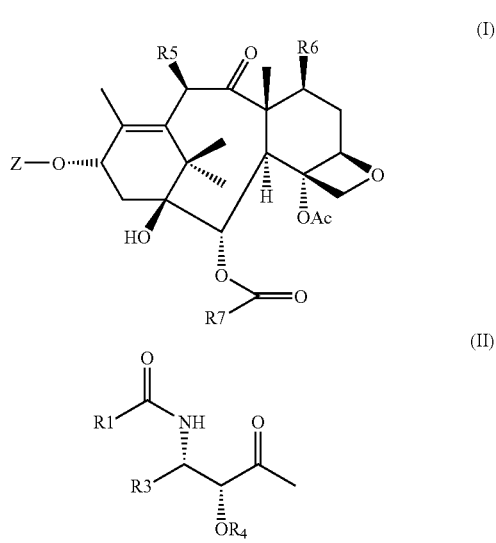

Z = H or a radical of formula II $R_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical. Preferably $R_1$ is —$OR_2$ or an optionally substituted aryl or heterocyclic radical $R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical. Preferably $R_2$ is an alkyl group and more preferably a substituted alkyl group such as a t-butyl group.

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms $R_4$ is H or a linker, or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxy-carbonyl, alkenyloxycarbonyl, alkynyloxycarbonyl, optionally substituted aryl or heterocyclyl, aroyl or heterocyclylcarbonyl, aryloxycarbonyl or heterocyclyl-oxycarbonyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_5$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{12}$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$=optionally substituted heterocyclic radical

The present invention will be more completely described with its 5 major embodiments.

Embodiment 1

$R_5$ is the Linking Group

Z is H or a radical of II $R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical $R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical Preferably, $R_1$ is t-butoxy, crotyl, dimethylacrylyl, isobutenyl, hexenyl, cyclopentenyl, cyclohexenyl, furyl, pyrrolyl, thienyl, thiazolyl, imidazolyl, pyridyl, morpholino, piperidino, piperazino, oxazolyl, indolyl, benzofuranyl or benzothienyl.

More preferably, $R_1$ is t-butoxy, isobutenyl, crotonyl, dimethyacrylyl, thienyl, thiazolyl or furyl $R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms Preferably, $R_3$ is crotyl, dimethylacrylyl, isobutenyl, hexenyl, cyclopentenyl, cyclohexenyl, furyl, pyrrolyl, thienyl, thiazolyl, imidazolyl, pyridyl, oxazolyl, indolyl, benzofuranyl or benzothienyl.

More preferably, $R_3$ is iso-butenyl, crotyl, dimethylacrylyl, thienyl, thiazolyl, pyridyl, tert-butyl, or furyl.

$R_4$ is H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

Most preferably, $R_4$ is H.

$R_5$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —O(CR$_{15}$R$_{16}$)$_m$(CR$_{17}$R$_{18}$)$_n$(OCH$_2$CH$_2$)$_y$ SZ', —OCO(CR$_{15}$R$_{16}$)$_m$(CR$_{17}$R$_{18}$)$_n$(OCH$_2$CH$_2$)$_y$ SZ', —O(CR$_{15}$R$_{16}$)$_m$(CR$_{19}$=CR$_{20}$)(CR$_{17}$R$_{18}$)$_m$(OCH$_2$CH$_2$)$_y$ SZ', OCO—(CR$_{15}$R$_{16}$)$_m$(CR$_{19}$=CR$_{20}$)(CR$_{17}$R$_{18}$)$_m$ (OCH$_2$CH$_2$)$_y$SZ', —OCONR$_{14}$(CR$_{15}$R$_{16}$)$_m$(CR$_{17}$R$_{18}$)$_n$ (OCH$_2$CH$_2$)$_y$SZ', —OCO-phenyl-X'SZ', —OCO-furyl-X'SZ', —OCO-oxazolyl-X'SZ', —OCO-thiazolyl-X'SZ', —OCO-thienyl-X'SZ', —OCO-imidazolyl-X'SZ', —OCO-morpholino-X'SZ', —OCO-piperazino-X'SZ', —OCO-piperidino-X'SZ' and —OCO—N-methylpiperazino-X'SZ', or —OCO—N-methylpiperazino-X'SZ', wherein:

Z' is H, SR', SCOR' or a thiol protective group, wherein X' is a direct link or a linear alkyl or branched alkyl having from 1-10 carbon atoms or a polyethylene glycol spacer with 2 to 20 repeating ethylene oxy units;

R' and $R_{14}$ are the same or different and are linear alkyl, branched alkyl or cyclic alkyl having from 1 to 10 carbon atoms, or simple or substituted aryl or heterocyclic, and $R_{14}$ can in addition be H, $R_{15}$, $R_{16}$, $R_{17}$ and $R_{18}$ are the same or different and are H or a linear or branched alkyl having from 1 to 4 carbon atoms, $R_{19}$ and $R_{20}$ are H or alkyl, n is an integer of 1 to 10, m is an integer from 1 to 10 and can also be 0, y is an integer from 1 to 20 and can also be 0.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$ is an optionally substituted heterocyclic radical

Preferably, $R_7$ is furyl, pyrrolyl, thienyl, thiazolyl, imidazolyl, pyridyl, indolyl, benzofuranyl or benzothienyl.

Embodiment 2

$R_1$ is the Linking Group

Z is a radical of II $R_1$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —(CR$_{15}$R$_{16}$)$_m$(CR$_{17}$R$_{18}$)$_n$(OCH$_2$CH$_2$)$_y$SZ', —O(CR$_{15}$R$_{16}$)$_m$(CR$_{17}$R$_{18}$)$_n$(OCH$_2$CH$_2$)$_y$SZ', —(CR$_{15}$R$_{16}$)$_m$(CR$_{19}$=CR$_{20}$)(CR$_{17}$R$_{18}$)$_m$(OCH$_2$CH$_2$)$_y$SZ', —O—(CR$_{15}$R$_{18}$)$_m$(CR$_{19}$=CR$_{20}$)(CR$_{17}$R$_{18}$)$_m$(OCH$_2$CH$_2$)$_y$SZ', NR$_{14}$(CR$_{15}$R$_{16}$)$_m$(CR$_{17}$R$_{18}$)$_n$(OCH$_2$CH$_2$)$_y$SZ', -phenyl-X'SZ', -furyl-X'SZ', -oxazolyl-X'SZ', thiazolyl-X'SZ', -thienyl-X'SZ', -imidazolyl-X'SZ', -morpholino-X'SZ', -piperazino-X'SZ', -piperidino-X'SZ' and —N-methylpiperazino-X'SZ', or —N-methylpiperazino-X'SZ', wherein:

Z' is H, SR', SCOR' or a thiol protective group, wherein X' is a direct link or a linear alkyl or branched alkyl having from 1-10 carbon atoms or a polyethylene glycol spacer with 2 to 20 repeating ethylene oxy units;

R' and $R_{14}$ are the same or different and are linear alkyl, branched alkyl or cyclic alkyl having from 1 to 10 carbon atoms, or simple or substituted aryl or heterocyclic, and $R_{14}$ can in addition be H, $R_{15}$, $R_{16}$, $R_{17}$ and $R_{18}$ are the same or different and are H or a linear or branched alkyl having from 1 to 4 carbon atoms, $R_{19}$ and $R_{20}$ are H or alkyl, n is an integer of 1 to 10, m is an integer from 1 to 10 and can also be 0, y is an integer from 1 to 20 and can also be 0.

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms Preferably, $R_3$ is crotyl, dimethylacrylyl, isobutenyl, hexenyl, cyclopentenyl, cyclohexenyl, furyl, pyrrolyl, thienyl, thiazolyl, imidazolyl, pyridyl, oxazolyl, indolyl, benzofuranyl or benzothienyl.

More preferably, $R_3$ is iso-butenyl, crotyl, dimethylacrylyl, thienyl, thiazolyl, pyridyl, tert-butyl, or furyl.

$R_4$ is H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

Most preferably, $R_4$ is H.

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$ is an optionally substituted heterocyclic radical

Preferably, $R_7$ is furyl, pyrrolyl, thienyl, thiazolyl, imidazolyl, pyridyl, indolyl, benzofuranyl or benzothienyl.

Embodiment 3

$R_3$ is the Linking Group

Z is a radical of II $R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical $R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical Preferably, $R_1$ is t-butoxy, crotyl, dimethylacrylyl, isobutenyl, hexenyl, cyclopentenyl, cyclohexenyl, furyl, pyrrolyl, thienyl, thiazolyl, imidazolyl, pyridyl, morpholino, piperidino, piperazino, oxazolyl, indolyl, benzofuranyl or benzothienyl.

More preferably, $R_1$ is t-butoxy, isobutenyl, crotonyl, dimethyacrylyl, thienyl, thiazolyl or furyl $R_3$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —(CR$_{15}$R$_{16}$)$_m$(CR$_{17}$R$_{18}$)$_n$(OCH$_2$CH$_2$)$_y$SZ', (CR$_{15}$R$_{16}$)$_m$(CR$_{19}$=CR$_{20}$)(CR$_{17}$R$_{18}$)$_m$(OCH$_2$CH$_2$)$_y$SZ', phenyl-X'SZ', furyl-X'SZ', oxazolyl-X'SZ', thiazolyl-X'SZ', thienyl-X'SZ', imidazolyl-X'SZ', wherein:

Z' is H, SR', SCOR' or a thiol protective group,

Wherein X' is a direct link or a linear alkyl or branched alkyl having from 1-10 carbon atoms or a polyethylene glycol spacer with 2 to 20 repeating ethylene oxy units R' is linear alkyl, branched alkyl or cyclic alkyl having from 1 to 10 carbon atoms, or simple or substituted aryl or heterocyclic, $R_{15}$, $R_{16}$, $R_{17}$ and $R_{18}$ are the same or different and are H or a linear or branched alkyl having from 1 to 4 carbon atoms, $R_{19}$ and $R_{20}$ are H or alkyl, n is an integer of 1 to 10, m is an integer from 1 to 10 and can also be 0, y is an integer from 1 to 20 and can also be 0.

$R_4$ is H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

Most preferably, $R_4$ is H.

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$ is an optionally substituted heterocyclic radical

Preferably, $R_7$ is furyl, pyrrolyl, thienyl, thiazolyl, imidazolyl, pyridyl, indolyl, benzofuranyl or benzothienyl.

Embodiment 4

$R_4$ is the Linking Group

Z is a radical of formula II $R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical $R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical Preferably, $R_1$ is t-butoxy, crotyl, dimethylacrylyl, isobutenyl, hexenyl, cyclopentenyl, cyclohexenyl, furyl, pyrrolyl, thienyl, thiazolyl, imidazolyl, pyridyl, morpholino, piperidino, piperazino, oxazolyl, indolyl, benzofuranyl or benzothienyl.

More preferably, $R_1$ is t-butoxy, isobutenyl, crotonyl, dimethyacrylyl, thienyl, thiazolyl or furyl $R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms Preferably, $R_3$ is crotyl, dimethylacrylyl, isobutenyl, hexenyl, cyclopentenyl, cyclohexenyl, furyl, pyrrolyl, thienyl, thiazolyl, imidazolyl, pyridyl, oxazolyl, indolyl, benzofuranyl or benzothienyl.

More preferably, $R_3$ is iso-butenyl, crotyl, dimethylacrylyl, thienyl, thiazolyl, pyridyl, tert-butyl, or furyl.

$R_4$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —$CO(CR_{15}R_{16})_m(CR_{17}R_{18})_n(OCH_2CH_2)_y SZ'$, —$CO—(CR_{15}R_{16})_m(CR_{19}=CR_{120})(CR_{17}R_{18})_m (OCH_2CH_2)_y SZ'$, —$CONR_{14}(CR_{15}R_{16})_m(CR_{17}R_{18})_n (OCH_2CH_2)_y SZ'$, CO-furyl-X'SZ', CO-thienyl-X'SZ', CO-thiazolyl-X'SZ' and —CO—N-methylpiperazino-X'SZ', —CO-morpholino-X'SZ', —CO-piperazino-X'SZ', —CO-piperidino-X'SZ', or —CO—N-methylpiperazino-X'SZ', wherein:

Z' is H, SR', SCOR' or a thiol protective group,

X' is a linear alkyl or branched alkyl having from 1-10 carbon atoms or a polyethylene glycol spacer with 2 to 20 repeating ethylene oxy units;

R' and $R_{14}$ are the same or different and are linear alkyl, branched alkyl or cyclic alkyl having from 1 to 10 carbon atoms, or simple or substituted aryl or heterocyclic, and $R_{14}$ can in addition be H, $R_{15}$, $R_{16}$, $R_{17}$ and $R_{18}$ are the same or different and are H or a linear or branched alkyl having from 1 to 4 carbon atoms, $R_{19}$ and $R_{20}$ are H or methyl, n is an integer of 1 to 10, m is an integer from 1 to 10 and can also be 0, y is an integer from 1 to 20 and can also be 0.

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —$OCONR_{10}R_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —$OCONR_{12}R_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$ is an optionally substituted heterocyclic radical

Preferably, $R_7$ is furyl, pyrrolyl, thienyl, thiazolyl, imidazolyl, pyridyl, indolyl, benzofuranyl or benzothienyl.

Embodiment 5

$R_6$ is the Linking Group

Z is H or a radical of II $R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical $R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical.

Preferably, $R_1$ is t-butoxy, crotyl, dimethylacrylyl, isobutenyl, hexenyl, cyclopentenyl, cyclohexenyl, furyl, pyrrolyl, thienyl, thiazolyl, imidazolyl, pyridyl, morpholino, piperidino, piperazino, oxazolyl, indolyl, benzofuranyl or benzothienyl.

More preferably, $R_1$ is t-butoxy, isobutenyl, crotonyl, dimethyacrylyl, thienyl, thiazolyl or furyl.

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms.

Preferably, $R_3$ is crotyl, dimethylacrylyl, isobutenyl, hexenyl, cyclopentenyl, cyclohexenyl, furyl, pyrrolyl, thienyl, thiazolyl, imidazolyl, pyridyl, oxazolyl, indolyl, benzofuranyl or benzothienyl.

More preferably, $R_3$ is iso-butenyl, crotyl, dimethylacrylyl, thienyl, thiazolyl, pyridyl, tert-butyl, or furyl.

$R_4$ is H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbdnyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

Most preferably, $R_4$ is H.

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —O(CR$_{15}$R$_{16}$)$_m$(CR$_{17}$R$_{18}$)$_n$(OCH$_2$CH$_2$)$_y$SZ', —OCO(CR$_{15}$R$_{16}$)$_m$(CR$_{17}$R$_{18}$)$_n$(OCH$_2$CH$_2$)$_y$SZ', —O(CR$_{15}$R$_{16}$)$_m$(CR$_{19}$=CR$_{20}$)(CR$_{17}$R$_{18}$)$_m$(OCH$_2$CH$_2$)$_y$SZ', —OCO—(CR$_{15}$R$_{16}$)$_m$(CR$_{19}$=CR$_{20}$)(CR$_{17}$R$_{18}$)$_m$(OCH$_2$CH$_2$)$_y$SZ', —OCONR$_{14}$(CR$_{15}$R$_{16}$)$_m$(CR$_{17}$R$_{18}$)$_n$(OCH$_2$CH$_2$)$_y$SZ', —OCO-phenyl-X'SZ', —OCO-furyl-X'SZ', —OCO-oxazolyl-X'SZ', —OCO-thiazolyl-X'SZ', —OCO-thienyl-X'SZ', —OCO-imidazolyl-X'SZ', —OCO-morpholino-X'SZ', —OCO-piperazino-X'SZ', —OCO-piperidino-X'SZ' and —OCO—N-methylpiperazino-X'SZ', or —OCO—N-methylpiperazino-X'SZ', wherein:

Z' is H, SR', SCOR' or a thiol protective group, wherein X' is a direct link or a linear alkyl or branched alkyl having from 1-10 carbon atoms or a polyethylene glycol spacer with 2 to 20 repeating ethylene oxy units;

R' and R$_{14}$ are the same or different and are linear alkyl, branched alkyl or cyclic alkyl having from 1 to 10 carbon atoms, or simple or substituted aryl or heterocyclic, and R$_{14}$ can in addition be H, R$_{15}$, R$_{16}$, R$_{17}$ and R$_{18}$ are the same or different and are H or a linear or branched alkyl having from 1 to 4 carbon atoms, R$_{19}$ and R$_{20}$ are H or alkyl, n is an integer of 1 to 10, m is an integer from 1 to 10 and can also be 0, y is an integer from 1 to 20 and can also be 0.

R$_7$ is an optionally substituted heterocyclic radical.

Preferably, R$_7$ is furyl, pyrrolyl, thienyl, thiazolyl, imidazolyl, pyridyl, indolyl, benzofuranyl or benzothienyl.

The present invention includes as a second embodiment the taxanes of formula (III) linked to a cell binding agent

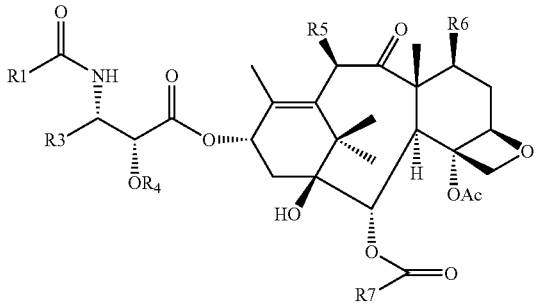

(III)

wherein R$_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical. Preferably R$_1$ is —OR$_2$ or an optionally substituted aryl or heterocyclic radical.

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical.

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms.

$R_4$ is H or a linker, or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxy-carbonyl, alkenyloxycarbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_5$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle such as unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl.

$R_7$=optionally substituted heterocyclic radical

Among the list of binding agents of the present invention can be cited antibodies, an antibody fragment, interferons, lymphokines, hormones, vitamins, growth factors, colony stimulating factors, and transferrin.

The preferred binding agent is chosen among the antibodies and more preferably the monoclonal antibodies. The cell binding agent can also be an antigen specific antibody fragment. The preferred antigen specific antibody fragments are chosen among sFV, Fab, Fab', or F(ab')$_2$. The cell binding agent can also be a growth factor or colony stimulating factor.

The fourth embodiment of the invention concerns a method of killing selected cell populations comprising contacting target cells or tissue containing target cells with an effective amount of the cytotoxic agent as previously described.

The present invention will be more completely described in the following examples which have not to be considered as a limitation of the invention.

Synthesis of 3'-dephenyl-3'-(2-furyl)-3'N-de-tert-butoxycarbonyl-3'N-(2-furoyl)-2-debenzoyl-2-(3-furoyl)-10-(4-methyldithiobutanoyl)-docetaxel

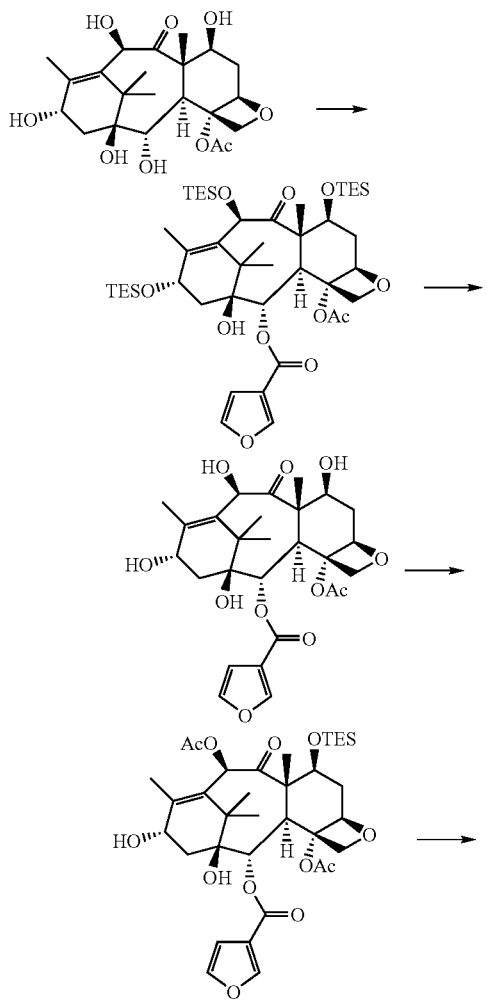

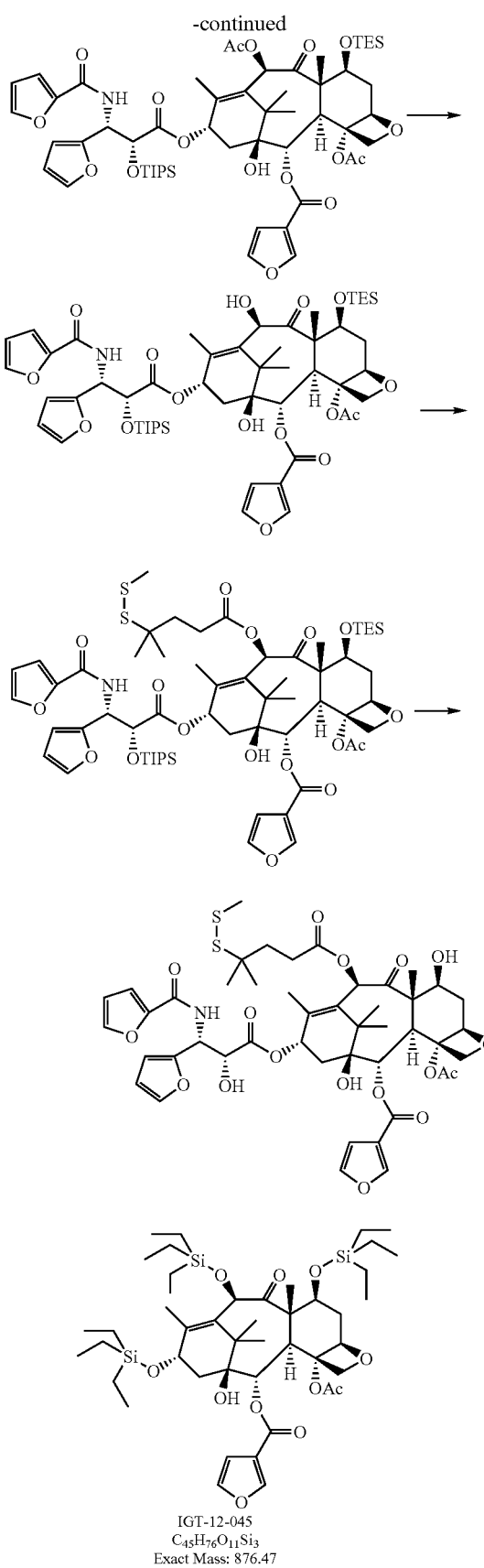

IGT-12-045
$C_{45}H_{76}O_{11}Si_3$
Exact Mass: 876.47

7,10,13-tri(triethylsilyloxy)-2-debenzoyl-2-(3-furoyl)-10-deacetyl baccatin III To a well stirred solution of 2-debenzoyl-10-deacetyl baccatin III (0.58 g, 0.74 mmol) in methylene chloride (12 mL) was added dimethylaminopyridine (DMAP) (0.54 g, 4.45 mmol) and 3-furoic acid (0.67 g, 6.0 mmol) followed by the addition of diisopropyl-carbodiimide (DIC) (0.9 mL, 5.7 mmol). The reaction was allowed to stir at room temperature overnight, after which it was complete. The reaction was extracted into ethyl acetate (2×50 mL) and the combined organic layers were washed with water (50 mL), saturated aqueous ammonium chloride (50 mL), water (50 mL), and brine (50 mL). The organic layer was dried over anhydrous sodium sulfate and concentrated in vacuo. The crude material was purified over silica gel using 20% ethyl acetate in hexane as the eluant. The fractions containing the desired product were pooled and concentrated to give 0.60 g of the title compound as a white solid. $^1$H NMR (CDCl$_3$) δ 0.63 (m, 18H), 0.99 (m, 27H), 1.14 (s, 3H), 1.18 (s, 3H), 1.64 (s, 3H), 1.89 (m, 1H), 1.98 (s, 3H), 2.11 (m, 2H), 2.25 (s, 3H), 2.53 (m, 1H), 3.81 (d, J=7.2 Hz, 1H), 4.17 (d, J=8.4 Hz, 1H), 4.37 (d, J=8.4 Hz, 1H), 4.41 (dd, J=6.8, 10.8 Hz, 1H), 4.94 (m, 2H), 5.19 (s, 1H), 5.51 (d, J=7.2 Hz, 1H), 6.77 (m, 1H), 7.46 (t, J=1.6 Hz, 1H), 8.04 (m, 1H). $^{13}$C NMR (CDCl$_3$) δ 5.1, 5.4, 6.2, 7.0, 7.1, 7.2, 10.6, 14.7, 20.8, 22.6, 26.5, 37.5, 39.9, 43.2, 47.0, 58.4, 66.4, 68.5, 72.9, 75.0, 76.0, 79.7, 81.0, 84.2, 110.0, 119.4, 136.0, 143.9, 144.2, 148.7, 163.7, 170.1, 205.8. m/z LC/MS for $C_{45}H_{76}O_{11}Si_3Na^+$: calcd: 899.5; found: 899.2

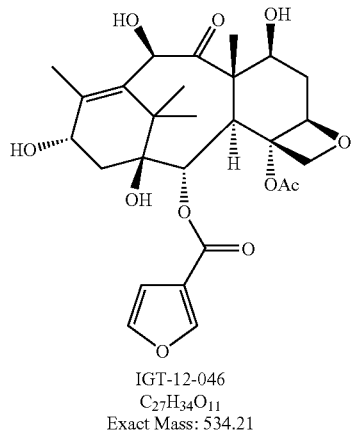

IGT-12-046
$C_{27}H_{34}O_{11}$
Exact Mass: 534.21

2-debenzoyl-2-(3-furoyl)-10-deacetyl baccatin III

A solution of 7,10,13-tri(triethylsilyloxy)-2-debenzoyl-2-(3-furoyl)-10-deacetyl baccatin III (2.05 g, 2.3 mmol) in anhydrous tetrahydrofuran (120 mL) was cooled to −30° C. Anhydrous pyridine (30 mL, 370 mmol) was added to the solution and the reaction was kept at −30° C. in a dry ice and acetone bath. HF/Pyridine (30 mL) was added dropwise and the reaction was allowed to stir with gradual warming to room temperature overnight. The reaction was quenched with saturated aqueous sodium bicarbonate and extracted into ethyl acetate (2×100 mL). The combined organic layers were washed with water (100 mL), then brine (100 mL), and dried over sodium sulfate and concentrated in vacuo. The crude material was triturated with hexane and decanted, then used without further purification. $^1$H NMR (CDCl$_3$) δ 1.07 (s, 3H), 1.09 (s, 3H), 1.73 (s, 3H), 2.06 (s, 3H), 1.83 (m, 1H), 2.02 (m, 1H), 2.19 (m, 1H), 2.25 (s, 3H), 2.60 (m, 1H), 3.49 (s, 1H), 3.96 (d, J=7.2 Hz, 1H), 4.19 (d, J=8.4 Hz, 1H), 4.27 (m, 1H), 4.40 (d, J=8.4 Hz, 1H), 4.86 (m, 1H), 4.98 (d, J=7.6 Hz, 1H), 5.24 (s, 1H), 5.52 (d, J=7.2 Hz, 1H), 6.77 (m, 1H), 7.47 (t, J=1.6 Hz, 1H), 8.07 (d, J=0.8 Hz, 1H). m/z LC/MS for $C_{27}H_{34}O_{11}Na^+$: calcd: 557.2; found: 557.1

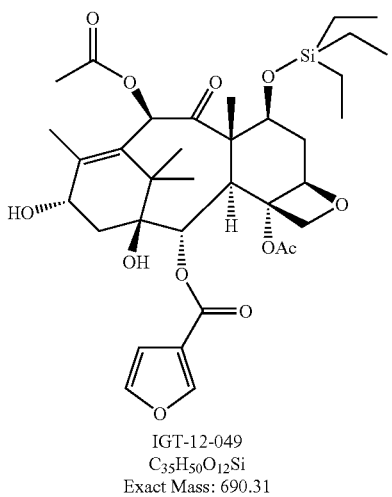

IGT-12-049
$C_{35}H_{50}O_{12}Si$
Exact Mass: 690.31

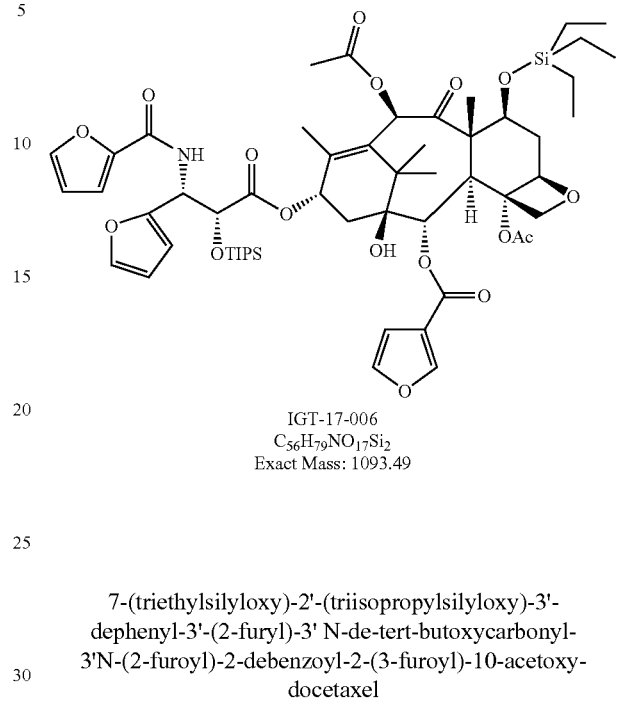

IGT-17-006
$C_{56}H_{79}NO_{17}Si_2$
Exact Mass: 1093.49

7-(triethylsilyloxy)-2'-(triisopropylsilyloxy)-3'-dephenyl-3'-(2-furyl)-3' N-de-tert-butoxycarbonyl-3'N-(2-furoyl)-2-debenzoyl-2-(3-furoyl)-10-acetoxy-docetaxel 7-Triethylsilyloxy-2-debenzoyl-2-(3-furoyl)-baccatin III To a mixture of 2-debenzoyl-2-(3-furoyl)-10-deacetyl baccatin III (1.02 g, 1.9 mmol) and imidazole (0.77 g, 11.3 mmol) in pyridine (10 ml) was added chlorotriethylsilane (0.56 g, 3.7 mmol) dropwise. The reaction was allowed to stir for 10 minutes at room temperature, after which it was observed by tlc to be complete. Acetic anhydride (3.5 mL, 37 mmol) was added dropwise to the mixture and the resulting mixture was stirred overnight at room temperature. The mixture was extracted into ethyl acetate (2×50 mL), and the combined organic layers were washed with water (50 mL), saturated aqueous sodium bicarbonate (2×50 mL), water (50 mL), then brine (50 mL). The organic layer was dried over anhydrous sodium sulfate and concentrated in vacuo. The crude material was purified over silica gel using 20% ethyl acetate in methylene chloride as the eluant. The fractions containing the desired product were pooled and concentrated to give 1.15 g of the title compound as a white solid. $^1$H NMR (CDCl$_3$) δ 0.58 (m, 6H), 0.92 (t, J=8.0 Hz, 9H), 1.04 (s, 3H), 1.17 (s, 3H), 1.64 (s, 1H), 1.66 (s, 3H), 1.87 (m, 1H), 2.10 (d, J=5.2 Hz, 1H), 2.17 (s, 6H), 2.21 (m, 1H), 2.24 (s, 3H), 2.52 (m, 1H), 3.83 (d, J=7.2 Hz, 1H), 4.17 (d, J=8.4 Hz, 1H), 4.38 (d, J=8.4 Hz, 1H), 4.47 (dd, J=6.8, 10.4 Hz, 1H), 4.82 (m, 1H), 4.96 (dd, J=1.6, 9.2 Hz, 1H), 5.51 (d, J=7.2 Hz, 1H), 6.44 (s, 1H), 6.77 (dd, J=0.8, 1.6 Hz, 1H), 7.46 (t, J=1.6 Hz, 1H), 8.07 (dd, J=0.8, 1.6 Hz, 1H). $^{13}$C NMR (CDCl$_3$) δ 5.5, 6.9, 10.1, 15.2, 20.2, 21.1, 22.9, 27.0, 37.4, 38.3, 42.9, 47.4, 58.8, 68.1, 72.5, 74.3, 75.9, 76.8, 78.9, 81.1, 84.4, 110.0, 119.2, 132.8, 144.1, 144.3, 148.8, 163.7, 169.6, 170.9, 202.3. m/z LC/MS for $C_{35}H_{50}O_{12}SiNa^+$: calcd: 713.3; found: 713.1

To a well stirred solution of 7-Triethylsilyloxy-2-debenzoyl-2-(3-furoyl)-baccatin III (145 mg, 0.2 mmol) and (3R, 4S)-1-(2-furoyl)-3-triisopropylsilyloxy-4-(2-furyl)-2-azetidinone (127 mg, 0.31 mmol) in dry THF (1.5 mL) was added a solution of 1.0 M LiHMDS in THF (0.32 mL, 0.32 mmol) dropwise at −40° C., and the solution was stirred at −40° C. for 1.5 hours. The reaction was quenched with saturated aqueous ammonium chloride (10 mL), and the aqueous layer was extracted with ethyl acetate (25 ml×3). The combined organic extracts were washed with water (25 mL), brine (25 mL), and dried over anhydrous sodium sulfate and concentrated in vacuo. The residue was purified by silica ptlc using 30% ethyl acetate in hexane as the developing solvent to afford 178 mg of the title compound as a white solid. $^1$H NMR (CDCl$_3$) δ 0.58 (m, 6H), 0.92 (t, 8.0 Hz, 9H), 1.00 (m, 21H), 1.16 (s, 3H), 1.18 (s, 3H), 1.68 (s, 3H), 1.90 (m, 1H), 2.00 (s, 3H), 2.12 (m, 1H), 2.16 (s, 3H), 2.30 (m, 1H), 2.45 (s, 3H), 2.52 (m, 1H), 3.79 (d, J=7.2 Hz, 1H), 4.24 (d, J=8.4 Hz, 1H), 4.38 (d, J=8.4 Hz, 1H), 4.47 (m, 1H), 4.93 (d, J=8.0 Hz, 1H), 5.08 (d, J=2.0 Hz, 1H), 5.57 (d, J=7.2 Hz, 1H), 5.74 (d, J=9.6 Hz, 1H), 6.19 (t, J=8.8 Hz, 1H), 6.25 (d, J=3.2 Hz, 1H), 6.34 (dd, J=1.6, 3.2 Hz, 1H), 6.43 (s, 1H), 6.48 (dd, J=1.6, 3.2 Hz, 1H), 6.81 (dd, J=0.8, 2.0 Hz, 1H), 7.05 (dd, J=0.8, 3.6 Hz, 1H), 7.13 (d, J=9.6 Hz, 1H), 7.38 (m, 1H), 7.46 (m, 2H), 8.25 (dd, J=0.8, 1.6 Hz, 1H). $^{13}$C NMR (CDCl$_3$) δ 5.3, 6.7, 10.1, 12.5, 14.3, 17.7, 20.9, 21.4, 22.9, 26.5, 35.6, 37.2, 43.2, 46.7, 50.9, 58.4, 71.2, 72.2, 72.9, 74.4, 75.0, 78.9, 81.1, 84.4, 107.8, 110.0, 110.8, 112.3, 115.1, 118.8, 133.5, 140.2, 142.1, 144.0, 144.5, 147.2, 149.2, 151.1, 157.8, 163.4, 169.3, 170.4, 170.9, 201.7. m/z LC/MS for $C_{56}H_{79}NO_{17}Si_2Na^+$: calcd: 1116.5; found: 1116.3

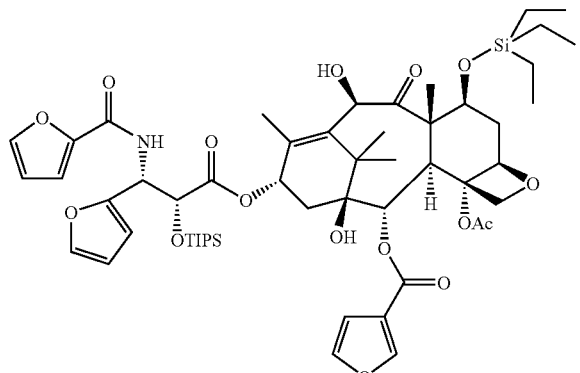

IGT-17-013
$C_{54}H_{77}NO_{16}Si_2$
Exact Mass: 1051.48

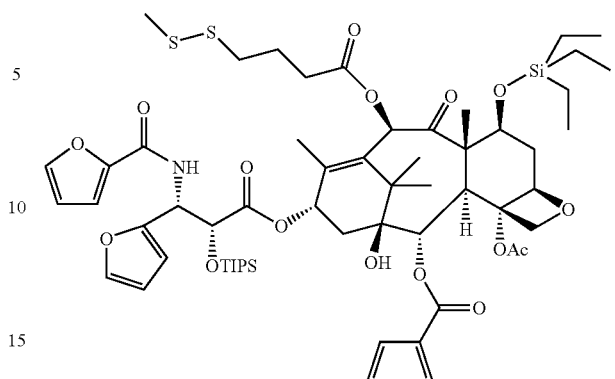

IGT-17-017
$C_{59}H_{85}NO_{17}S_2Si_2$
Exact Mass: 1199.48

7-(triethylsilyloxy)-2'-(triisopropylsilyloxy)-3'-dephenyl-3'-(2-furyl)-3' N-de-tert-butoxycarbonyl-3'N-(2-furoyl)-2-debenzoyl-2-(3-furoyl)-docetaxel To a solution of 7-(triethylsilyloxy)-2'-(triisopropylsilyloxy)-3'-dephenyl-3'-(2-furyl)-3'N-de-tert-butoxycarbonyl-3'N-(2-furoyl)-2-debenzoyl-2-(3-furoyl)-10-acetoxy-docetaxel (162 mg, 0.15 mmol) in ethanol (14 mL) was added hydrazine monohydrate (0.8 mL) at room temperature. After 10 minutes a second portion of hydrazine monohydrate was added (0.8 mL). The reaction was stirred at rt and monitored by tlc. After 14 hours the reaction was complete by tlc and quenched with saturated aqueous ammonium chloride (10 mL). The aqueous layer was extracted with ethyl acetate (50 ml×2). The combined organic extracts were washed with water (50 mL), brine (50 mL), and dried over anhydrous sodium sulfate and concentrated in vacuo. The residue was purified by silica ptlc using a mixture of 50% ether, 40% hexane, and 10% ethyl acetate as the developing solvent to afford 97 mg of the title compound as a white solid. $^1$H NMR (CDCl$_3$) δ 0.54 (m, 6H), 0.95 (m, 30H), 1.04 (s, 3H), 1.17 (s, 3H), 1.72 (s, 3H), 1.87 (m, 1H), 1.92 (s, 3H), 2.09 (m, 1H), 2.25 (m, 1H), 2.45 (m, 4H), 3.83 (d, J=7.2 Hz, 1H), 4.24 (m, 2H), 4.38 (m, 2H), 4.91 (d, J=8.0 Hz, 1H), 5.07 (d, J=1.2 Hz, 1H), 5.08 (s, 1H), 5.52 (d, J=7.2 Hz, 1H), 5.73 (d, J=9.6 Hz, 1H), 6.24 (m, 2H), 6.33 (dd, J=1.6, 3.2 Hz, 1H), 6.46 (dd, J=1.6, 3.2 Hz, 1H), 6.80 (d, J=1.6 Hz, 1H), 7.03 (d, J=3.2 Hz, 1H), 7.14 (d, J=9.6 Hz, 1H), 7.37 (s, 1H), 7.45 (m, 2H), 8.26 (s, 1H). $^{13}$C NMR (CDCl$_3$) δ 5.2, 6.7, 10.1, 12.4, 14.3, 17.7, 20.9, 22.8, 26.6, 36.0, 37.2, 43.1, 46.4, 50.9, 57.7, 71.3, 72.8, 72.9, 74.0, 74.5, 76.7, 79.0, 80.9, 84.4, 107.7, 110.0, 110.8, 112.3, 115.1, 118.8, 135.9, 138.1, 142.1, 144.0, 144.5, 147.1, 149.2, 151.1, 157.8, 163.3, 170.6, 170.8, 209.8. m/z LC/MS for $C_{54}H_{77}NO_{16}Si_2Na^+$: calcd: 1074.5; found: 1074.6

7-(triethylsilyloxy)-2'-(triisopropylsilyloxy)-3'-dephenyl-3'-(2-furyl)-3'N-de-tert-butoxycarbonyl-3' N-(2-furoyl)-2-debenzoyl-2-(3-furoyl)-10-(4-methyldithiobutanoyl)-docetaxel To a solution of 7-(triethylsilyloxy)-2'-(triisopropylsilyloxy)-3'-dephenyl-3'-(2-furyl)-3'N-de-tert-butoxycarbonyl-3'N-(2-furoyl)-2-debenzoyl-2-(3-furoyl)-docetaxel (95 mg, 0.09 mmol) in methylene chloride (3 mL) was added DMAP (22 mg) and 4-methyldithio-butanoic acid (160 mg, 0.89 mmol). To this mixture was then added DIC (0.14 mL, 0.89 mmol) and the resulting mixture stirred overnight. Upon completion, the reaction was quenched with saturated aqueous ammonium chloride (10 mL) and extracted into methylene chloride (10 ml×3). The combined organic extracts were dried over anhydrous sodium sulfate and concentrated in vacuo. The residue was purified by silica ptlc using 30% ethyl acetate in hexane as the developing solvent to afford 154 mg of the title compound as a white solid. $^1$H NMR (CDCl$_3$) δ 0.52 (m, 6H), 0.86 (t, J=8.0 Hz, 9H), 0.94 (m, 21H), 1.09 (s, 3H), 1.13 (s, 3H), 1.61 (s, 3H), 1.83 (m, 1H), 1.95 (s, 3H), 1.99 (m, 2H), 2.12 (m, 2H), 2.35 (s, 3H), 2.38 (s, 3H), 2.47 (m, 1H), 2.52 (t, J=7.2 Hz, 2H), 2.67 (m, 2H), 3.73 (d, J=6.8 Hz, 1H), 4.18 (d, J=8.4 Hz, 1H), 4.30 (d, J=8.4 Hz, 1H), 4.40 (dd, J=6.4, 10.0 Hz, 1H), 4.88 (d, J=8.8 Hz, 1H), 5.03 (s, 1H), 5.52 (d, J=6.8 Hz, 1H), 5.68 (d, J=9.6 Hz, 1H), 6.11 (t, J=8.4 Hz, 1H), 6.20 (d, J=2.8 Hz, 1H), 6.29 (t, J=2.8 Hz, 1H), 6.40 (s, 1H), 6.44 (dd, J=1.6, 3.2 Hz, 1H), 6.73 (d, J=1.6 Hz, 1H), 7.02 (d, J=3.2 Hz, 1H), 7.14 (d, J=9.6 Hz, 1H), 7.34 (s, 1H), 7.41 (s, 1H), 7.43 (s, 1H), 8.14 (s, 1H). $^{13}$C NMR (CDCl$_3$) δ 5.4, 6.8, 10.1, 12.4, 14.3, 17.8, 20.9, 22.5, 23.2, 24.0, 24.2, 26.5, 32.3, 32.7, 37.0, 43.2, 46.6, 51.1, 58.4, 71.4, 72.2, 72.8, 74.4, 75.0, 76.6, 78.4, 81.1, 84.3, 107.8, 110.0, 110.9, 112.4, 115.6, 118.9, 133.7, 140.1, 142.2, 144.0, 144.8, 146.7, 149.0, 150.9, 158.2, 163.1, 170.9, 171.2, 173.5, 201.7. m/z LC/MS for $C_{59}H_{85}NO_{17}S_2Si_2Na^+$: calcd: 1222.5; found: 1222.6

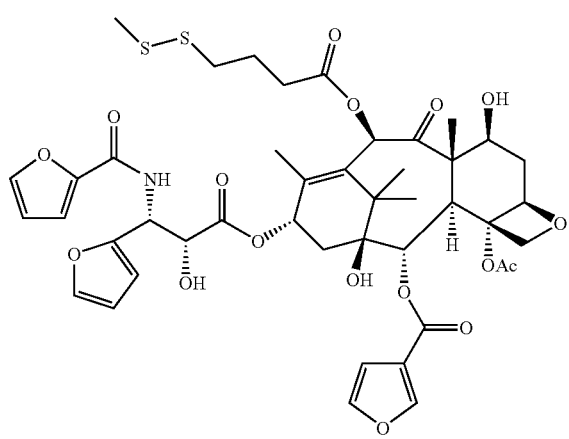

IGT-17-020
C44H51NO17S2
Exact Mass: 929.26

3'-dephenyl-3'-(2-furyl)-3' N-de-tert-butoxycarbonyl-3'N-(2-furoyl)-2-debenzoyl-2-(3-furoyl)-10-(4-methyldithiobutanoyl)-docetaxel To a solution of 7-(triethylsilyloxy)-2'-(triisopropylsilyloxy)-3'-dephenyl-3'-(2-furyl)-3'N-de-tert-butoxycarbonyl-3'N-(2-furoyl)-2-debenzoyl-2-(3-furoyl)-1-(4-methyldithiobutanoyl)-docetaxel (154 mg, 0.13 mmol) in pyridine-acetonitrile (1/1, 5.0 mL) was added HF/pyridine (70:30, 1.5 mL) at 0° C. The resulting mixture was stirred for 24 hours with gradual warming to room temperature. The reaction was quenched with saturated aqueous sodium bicarbonate (10 mL) and then extracted with ethyl acetate (2×20 mL). The combined organic layers were washed with water (15 mL) and brine (15 mL), dried over anhydrous sodium sulfate and concentrated in vacuo. The residue was purified by silica ptlc using 60% ethyl acetate in hexane as the developing solvent to afford 54 mg of the title compound as a white solid.

$^1$H NMR (CDCl$_3$) δ 1.09 (s, 3H), 1.21 (s, 3H), 1.65 (s, 3H), 1.84 (s, 3H), 1.87 (m, 1H), 2.12 (m, 2H), 2.27 (m, 2H), 2.38 (s, 3H), 2.40 (s, 3H), 2.52 (m, 1H), 2.66 (m, 2H), 2.81 (m, 2H), 3.65 (m, 1H) 3.75 (d, J=7.2 Hz, 1H), 4.23 (d, J=8.4 Hz, 1H), 4.36 (d, J=8.4 Hz, 1H), 4.40 (dd, J=6.4, 10.8 Hz, 1H), 4.81 (d, J=2.0 Hz, 1H), 4.93 (dd, J=1.6, 9.2 Hz, 1H), 5.54 (d, J=7.2 Hz, 1H), 5.82 (dd, J=2.0, 9.6 Hz, 1H), 6.23 (t, J=8.8 Hz, 1H), 6.27 (s, 1H), 6.38 (m, 2H), 6.47 (dd, J=1.6, 3.6 Hz, 1H), 6.80 (d, J=1.6 Hz, 1H), 7.07 (m, 2H), 7.42 (t, J=1.2 Hz, 1H), 7.45 (dd, J=0.8, 1.6 Hz, 1H), 7.47 (t, J=1.6 Hz, 1H), 8.24 (d, J=0.8 Hz, 1H). $^{13}$C NMR (CDCl$_3$) δ 9.8, 14.9, 22.2, 22.7, 23.3, 24.1, 24.3, 27.0, 32.2, 32.7, 37.0, 43.3, 45.7, 49.6, 58.7, 71.7, 72.2, 72.4, 74.7, 75.7, 76.7, 79.2, 81.2, 84.7, 108.1, 110.1, 110.9, 112.6, 115.8, 118.9, 133.2, 142.1, 142.9, 144.3, 144.8, 146.9, 149.4, 150.8, 158.1, 163.5, 170.6, 172.4, 173.3, 203.7. m/z LC/MS for C$_{44}$H$_{51}$NO$_{17}$S$_2$Na$^+$: calcd: 952.3; found: 952.3

Synthesis of 3'-dephenyl-3'-(2-furyl)-2-debenzoyl-2-(3-furoyl)-10-(4-methyldithiobutanoyl)-docetaxel

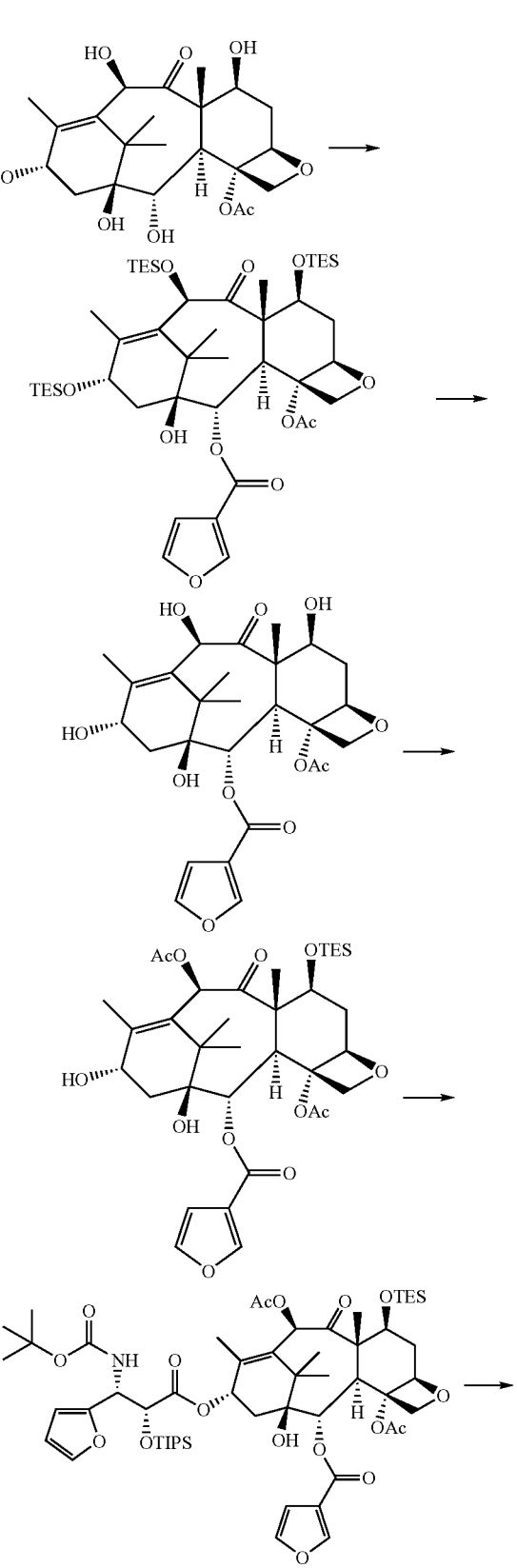

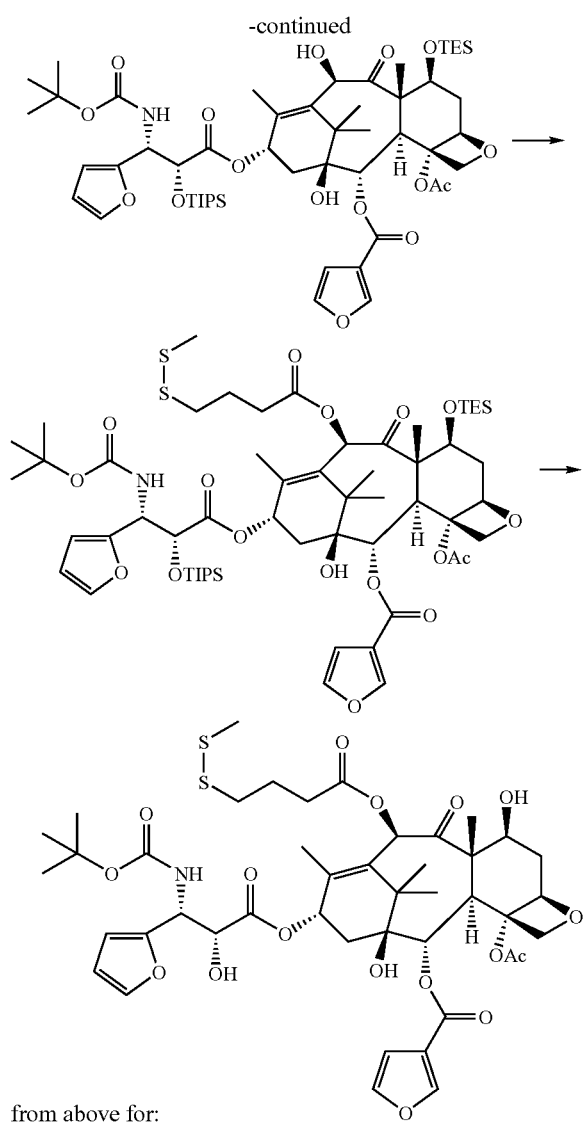

from above for:
7,10,13-tri(triethylsilyloxy)-2-debenzoyl-2-(3-furoyl)-10-deacetyl baccatin III 2-debenzoyl-2-(3-furoyl)-10-deacetyl baccatin III 7-Triethylsilyloxy-2-debenzoyl-2-(3-furoyl)-baccatin III

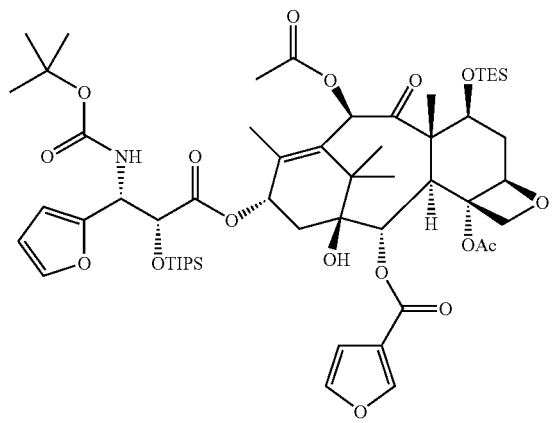

7-(triethylsilyloxy)-2'-(triisopropylsilyloxy)-3'-dephenyl-3'-(2-furyl)-2-debenzoyl-2-(3-furoyl)-10-acetoxy-docetaxel To a well stirred solution of 7-Triethylsilyloxy-2-debenzoyl-2-(3-furoyl)-baccatin III (361 mg, 0.52 mmol) and (3R, 4S)-1-(tert-butoxycarbonyl)-3-triisopropylsilyloxy-4-(2-furyl)-2-azetidinone (300 mg, 0.73 mmol) in dry THF (3.6 mL) was added a solution of 1.0 M LiHMDS in THF (0.732 mL, 0.73 mmol) dropwise at −40° C., and the solution was stirred at −40° C. for 3 hours. The reaction was quenched with saturated aqueous ammonium chloride (10 mL), and the aqueous layer was extracted with ethyl acetate (15 ml×2). The combined organic extracts were dried over anhydrous magnesium sulfate and concentrated in vacuo. The crude material was purified over silica gel using 30% ethyl acetate in hexane as the eluant. The fractions containing the desired product were pooled and concentrated to give 559 mg of the title compound as a white solid. $^1$H NMR (CDCl$_3$) δ 0.58 (m, 6 H), 0.94 (m, 30 H), 1.19 (s, 3 H), 1.20 (s, 3 H), 1.36 (s, 9 H), 1.68 (s, 3 H), 1.90 (m, 1 H), 2.03 (s, 3 H), 2.17 (s, 3 H), 2.24 (m, 2 H), 2.42 (s, 3 H), 2.52 (m, 1 H), 3.80 (d, J=8.8 Hz, 1 H), 4.21 (d, J=8.4 Hz, 1 H), 4.38 (d, J=8.4 Hz, 1 H), 4.47 (dd, J=6.4, 10.4 Hz, 1 H), 4.93 (d, J=8.8 Hz, 1 H), 4.97 (d, J=0.8 Hz, 1 H), 5.26 (d, J=10.0 Hz, 1 H), 5.32 (d, J=10.0 Hz, 1 H), 5.56 (d, J=7.2 Hz, 1 H), 6.20 (t, J=9.2 Hz, 1 H), 6.24 (d, J=3.2 Hz, 1 H), 6.34 (dd, J=2.0, 3.2 Hz, 1 H), 6.45 (s, 1 H), 6.79 (s, 1 H), 7.35 (s, 1 H), 7.43 (m, 1 H), 8.15 (s, 1 H). $^{13}$C NMR (CDCl$_3$) δ 5.6, 7.1, 10.4, 12.8, 14.7, 18.10, 18.12, 21.2, 21.6, 23.2, 26.7, 28.4, 35.7, 37.5, 43.6, 47.1, 53.5, 58.7, 71.6, 72.6, 73.4, 74.7, 75.4, 79.2, 80.6, 81.4, 84.7, 107.8, 110.3, 111.1, 119.1, 133.6, 141.0, 142.2, 144.4, 149.4, 152.3, 155.8, 163.8, 169.6, 170.6, 171.6, 202.2. m/z LCMS for C$_{56}$H$_{85}$NO$_{17}$Si$_2$Na$^+$: calcd: 1122.5; found: 1122.4.

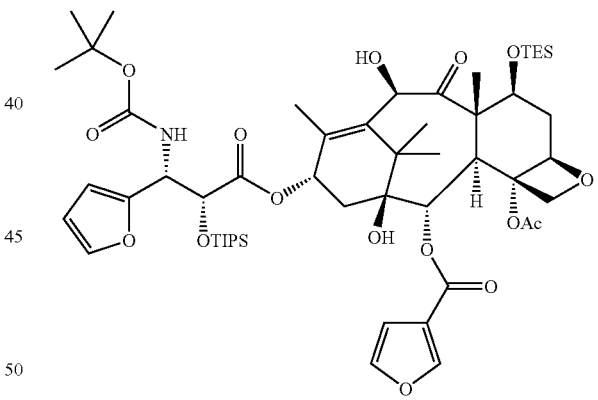

7-(triethylsilyloxy)-2'-(triisopropylsilyloxy)-3'-dephenyl-3'-(2-furyl)-2-debenzoyl-2-(3-furoyl)-docetaxel To a solution of 7-(triethylsilyloxy)-2'-(triisopropylsilyloxy)-3'-dephenyl-3'-(2-furyl)-2-debenzoyl-2-(3-furoyl)-10-acetoxy-docetaxel (559 mg, 0.51 mmol) in ethanol (15 mL) was added dropwise hydrazine monohydrate (5.96 mL) at room temperature. The reaction was stirred at rt and monitored by tlc. After 1 hour the reaction was complete by tlc and quenched with saturated aqueous ammonium chloride (10 mL). The aqueous layer was extracted with ethyl acetate (15 ml×2). The combined extracts were dried over anhydrous magnesium sulfate and concentrated in vacuo. The residue was purified by silica ptlc using a mixture of 50% ether, 40% hexane, and 10% ethyl acetate as the developing solvent to afford 199 mg of the title compound as a white solid. $^1$H NMR (CDCl$_3$) δ 0.54 (m, 6 H), 0.95 (m, 30 H), 1.07 (s, 3 H), 1.22 (s, 3 H), 1.35 (s, 9 H), 1.72 (s, 3 H), 1.92, (m, 1 H), 1.93 (s, 3 H), 2.21 (m, 2 H), 2.41 (s, 3 H), 2.46 (m, 1 H), 3.85 (d, J=7.2 Hz, 1 H), 4.22 (d, J=8.4 Hz, 1 H), 4.24 (d, J=2.0 Hz, 1 H), 4.38 (m, 2 H) 4.92 (d, J=8.0 Hz, 1 H), 4.94 (d, J=5.6 Hz, 1 H), 5.10 (d, J=2.0 Hz, 1 H), 5.27 (d, J=10.0 Hz, 1 H), 5.31 (d, J=10.0 Hz, 1 H), 5.52 (d, J=7.2 Hz, 1 H), 6.23 (d, J=2.8 Hz, 1 H), 6.26 (t, J=8.8 Hz, 1 H), 6.33 (dd, J=2.0, 3.2 Hz, 1 H), 6.78 (d, J=1.2 Hz, 1 H), 7.34 (d, J=1.2 Hz, 1 H), 7.42 (t, J=1.6 Hz, 1 H), 8.15 (s, 1 H). $^{13}$C NMR (CDCl$_3$) δ 5.5, 7.1, 10.4, 12.7, 14.7, 18.07, 18.11, 21.1, 23.1, 26.8, 28.4, 36.1, 37.5, 43.5, 46.8, 53.4, 58.1, 71.6, 73.2, 73.4, 74.4, 74.8, 79.3, 80.6, 81.3, 84.7, 107.8, 110.3, 111.1, 119.1, 136.1, 138.8, 142.2, 144.3, 149.4, 152.4, 155.8, 163.7, 170.7, 171.5, 210.2. m/z LCMS for C$_{54}$H$_{83}$NO$_{16}$Si$_2$Na$^+$: calcd: 1080.5; found: 1080.3.

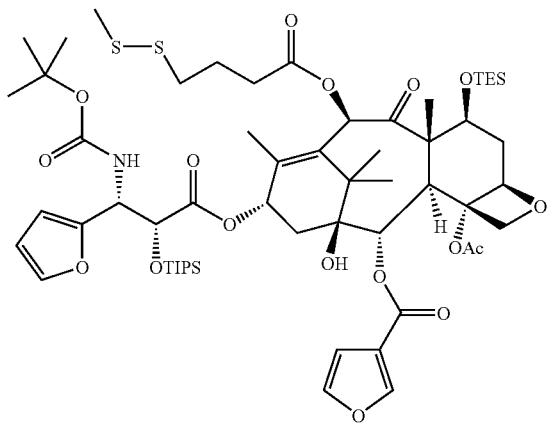

7-(triethylsilyloxy)-2'-(triisopropylsilyloxy)-3'-dephenyl-3'-(2-furyl)-2-debenzoyl-2-(3-furoyl)-10-(4-methyldithiobutanoyl)-docetaxel To a solution of 7-(triethylsilyloxy)-2'-(triisopropylsilyloxy)-3'-dephenyl-3'-(2-furyl)-2-debenzoyl-2-(3-furoyl)-docetaxel (199 mg, 0.188 mmol) in methylene chloride (4.1 mL) was added DMAP (23 mg) and 4-methyldithio-butanoic acid (313 mg, 1.88 mmol). To this mixture was then added DIC (0.294 mL, 1.88 mmol) and the resulting mixture stirred overnight. Upon completion, the reaction was quenched with saturated aqueous ammonium chloride (10 mL) and extracted into methylene chloride (10 ml×2). The combined organic extracts were dried over anhydrous sodium sulfate and concentrated in vacuo. The residue was purified by silica ptlc using 20% ethyl acetate in hexane as the developing solvent to afford 135 mg of the title compound as a white solid. $^1$H NMR (CDCl$_3$) δ 0.56 (m, 6 H), 0.95 (m, 30 H), 1.18 (s, 3 H), 1.34 (s, 12 H), 1.66 (s, 3 H), 1.90 (m, 1 H), 2.01 (s, 3 H), 2.10 (m, 2 H), 2.24 (m, 2 H), 2.38 (s, 3 H), 2.42 (s, 3 H), 2.72 (m, 2 H), 2.82 (m, 2 H), 3.79 (d, J=7.2 Hz, 1 H), 4.20 (d, J=8.4 Hz, 1 H), 4.36 (d, J=8.4 Hz, 1 H), 4.46 (dd, J=6.4, 10.4 Hz, 1 H), 4.92 (d, J=8.4 Hz, 1 H), 4.96 (d, J=1.2 Hz, 1 H), 5.25 (d, J=10.0 Hz, 1 H), 5.30 (d, J=10.0 Hz, 1 H), 5.55 (d, J=7.2 Hz, 1 H), 6.18 (t, J=8.8 Hz, 1 H), 6.22 (d, J=3.2 Hz, 1 H), 6.32 (dd, J=1.6, 3.2 Hz, 1 H), 6.47 (s, 1 H), 6.77 (d, J=1.2 Hz, 1 H), 7.34 (s, 1 H), 7.42 (t, J=1.6 Hz, 1 H), 8.13 (s, 1 H). $^{13}$C NMR (CDCl$_3$) δ 5.7, 7.1, 10.4, 12.7, 14.7, 18.07, 18.08, 22.9, 23.1, 23.4, 23.5, 24.6, 26.7, 28.4, 32.9, 35.7, 37.2, 43.5, 47.0, 53.5, 58.7, 71.6, 72.5, 73.4, 74.7, 75.3, 76.9, 79.1, 80.6, 81.4, 84.6, 107.8, 110.3, 111.1, 119.1, 133.6, 140.9, 142.2, 144.3, 149.3, 152.3, 155.8, 163.7, 170.6, 171.4, 171.6, 202.0. m/z LCMS for C$_{59}$H$_{91}$NO$_{17}$S$_2$Si$_2$Na$^+$: calcd: 1228.5; found: 1228.2.

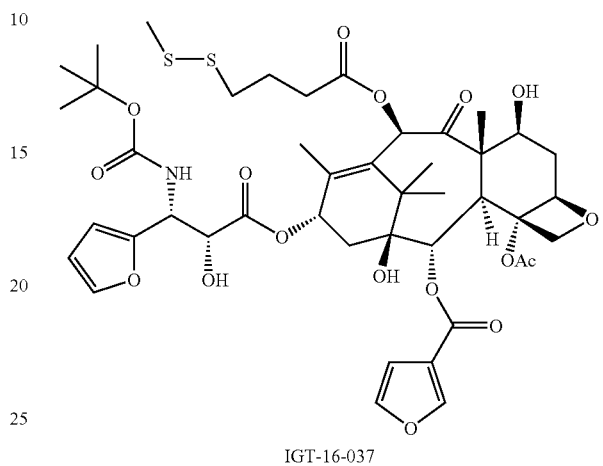

IGT-16-037

3'-dephenyl-3'-(2-furyl)-2-debenzoyl-2-(3-furoyl)-1-(4-methyldithio-butanoyl)-docetaxel To a solution of 7-(triethylsilyloxy)-2'-(triisopropylsilyloxy)-3'-dephenyl-3'-(2-furyl)-2-debenzoyl-2-(3-furoyl)-10-(4-methyldithiobutanoyl)-docetaxel (135 mg, 0.112 mmol) in pyridine-acetonitrile (1/1, 2.7 mL) was added HF/pyridine (70:30, 1.25 mL) at 0° C. The resulting mixture was stirred for 24 hours with gradual warming to room temperature. The reaction was quenched with saturated aqueous sodium bicarbonate (10 mL) and then extracted with ethyl acetate (2×20 mL). The combined organic layers were washed with water (15 mL) and brine (15 mL), dried over anhydrous sodium sulfate and concentrated in vacuo. The residue was purified by silica ptlc using 60% ethyl acetate in hexane as the developing solvent to afford 31.4 mg of the title compound as a white solid. $^1$H NMR (CDCl$_3$) δ 1.11 (s, 3 H), 1.25 (s, 3 H), 1.36 (s, 9 H), 1.66 (s, 3 H), 1.87 (m, 1 H), 1.88 (s, 3 H), 2.14 (p, J=7.2 Hz, 2 H), 2.28 (dd, J=4.4, 8.8 Hz, 2 H), 2.36 (s, 3 H), 2.42 (s, 3 H), 2.49 (d, J=4.4 Hz, 1 H), 2.65 (m, 2 H), 2.82 (m, 2 H), 3.29 (d, J=5.6 Hz, 1 H), 3.77 (d, J=7.2 Hz, 1H), 4.20 (d, J=8.4 Hz, 1 H), 4.38 (d, J=8.4 Hz, 1 H), 4.41 (m, 1 H), 4.71 (dd, J=1.6, 5.2 Hz, 1 H), 4.95 (d, J=8.0 Hz, 1 H), 5.24 (d, J=10.0 Hz, 1 H), 5.34 (d, J=10.0 Hz, 1 H), 5.54 (d, J=7.2 Hz, 1 H), 6.24 (t, J=8.8 Hz, 1 H), 6.29 (s, 1 H), 6.31 (d, J=3.2 Hz, 1 H), 6.37 (dd, J=2.0, 3.2 Hz, 1 H), 6.79 (d, J=1.6 Hz, 1H), 7.40 (d, J=1.2 Hz, 1 H), 7.45 (t, J=1.6 Hz, 1 H), 8.15 (s, 1 H). $^{13}$C NMR (CDCl$_3$) δ 9.9, 15.2, 22.3, 22.9, 23.5, 24.5, 27.0, 28.4, 32.9, 35.8, 35.9, 37.1, 43.5, 45.9, 51.9, 58.9, 72.0, 72.5, 72.8, 74.8, 75.9, 76.8, 79.5, 80.9, 81.4, 84.8, 107.8, 110.2, 111.0, 119.0, 133.3, 142.7, 142.8, 144.5, 149.4, 151.6, 155.4, 163.8, 170.6, 173.0, 173.5, 203.9. m/z LCMS for C$_{44}$H$_{57}$NO$_{17}$S$_2$Na$^+$: calcd: 958.3; found: 958.1.

Synthesis of 3'-dephenyl-3'-(2-furyl)-2-debenzoyl-2-(2-thienyl)-10-(4-methyldithiobutanoyl)-docetaxel

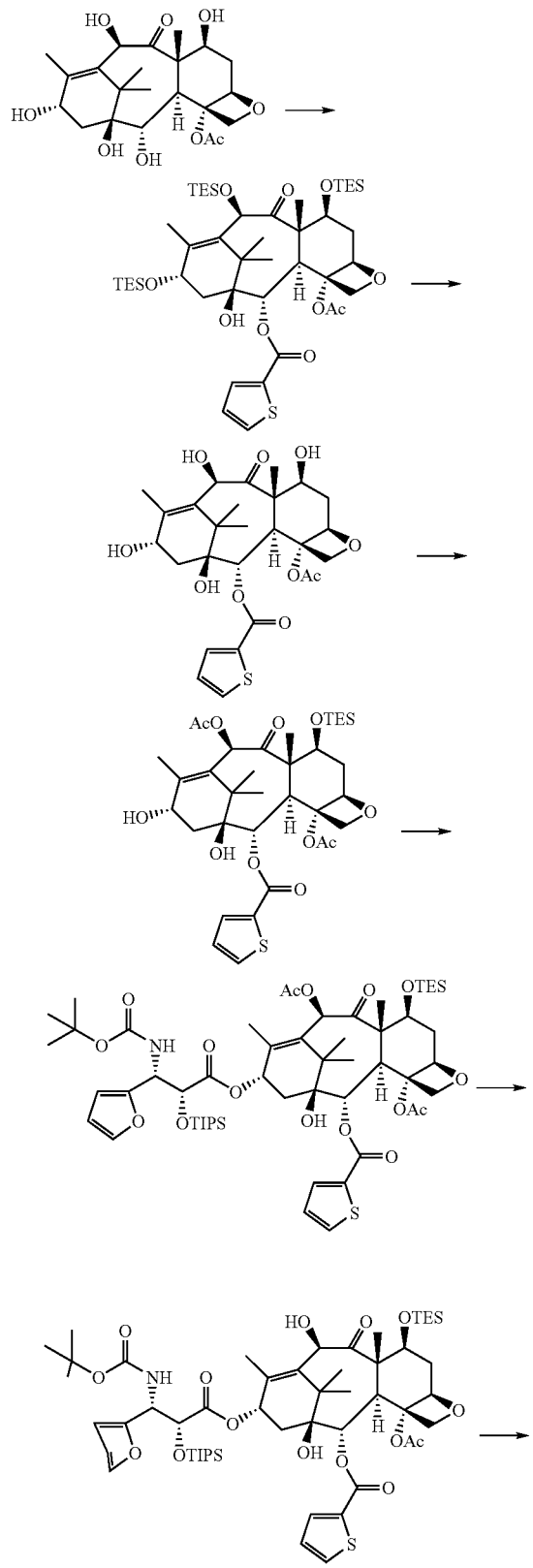

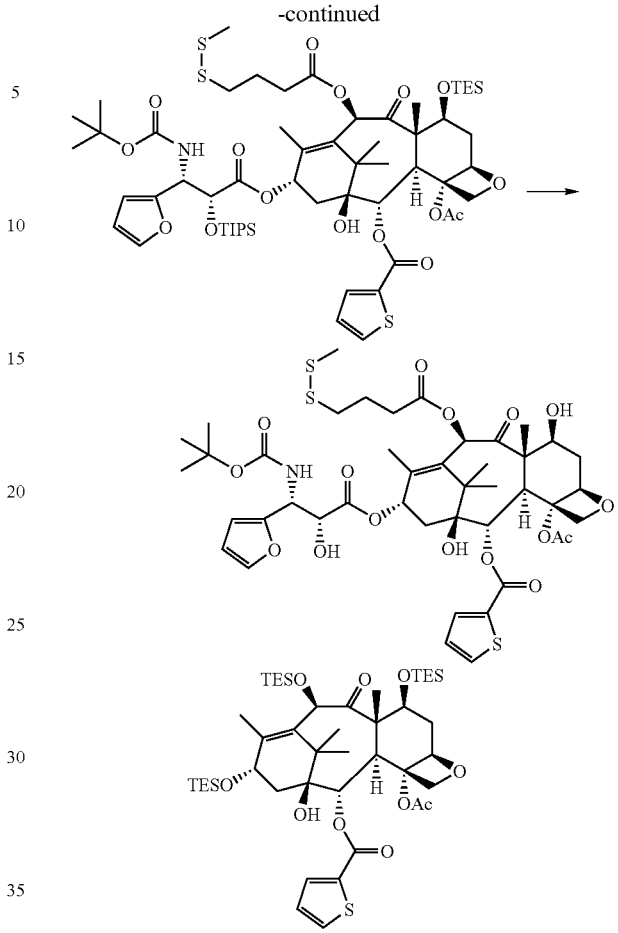

7,10,13-Tri(triethylsilyloxy)-debenzoyl-2-(2-thienoyl)baccatin III

To a well stirred solution 2-debenzoyl-10-deacetyl baccatin III (6.28 g, 8.03 mmol) in methylene chloride (210 mL) was added dimethylaminopyridine (DMAP) (5.89 g, 48.2 mmol) and 2-thiophene carboxylic acid (10.3 g, 80.3 mmol) followed by the addition of diisopropylcarbodiimide (DIC) (10.1 g, 80.3 mmol). The reaction was allowed to stir at room temperature for 2 days, after which it was complete. The reaction was diluted with methylene chloride (50 mL), washed with water (50 mL), saturated aqueous ammonium chloride (50 mL), water (50 mL), and brine (50 mL). The organic layer was dried over anhydrous sodium sulfate and concentrated in vacuo. The crude material was purified over silica gel using 20% ethyl acetate in hexane as the eluant. The fractions containing the desired product were pooled and concentrated to give 6.38 g of the title compound as a white solid. $^1$H NMR (CDCl$_3$) δ 0.64 (m, 18 H), 0.97 (m, 27 H), 1.12 (s, 3 H), 1.17 (s, 3 H), 1.65 (s, 3 H), 1.90 (m, 1 H), 1.97 (s, 3 H), 2.11 (m, 2 H), 2.26 (s, 3 H), 2.52 (m, 1 H), 3.81 (d, J=7.2 Hz, 1 H), 4.21 (d, J=8.4 Hz, 1 H), 4.39 (m, 2 H), 4.92 (m, 2 H), 5.18 (s, 1 H), 5.52 (d, J=7.2 Hz, 1 H), 7.12 (dd, J=3.6, 4.8 Hz, 1 H), 7.61 (dd, J=1.2, 5.2 Hz, 1 H), 7.84 (dd, J=1.2, 3.6 Hz, 1 H). $^{13}$C NMR (CDCl$_3$) δ 5.2, 5.6, 6.3, 7.2, 7.27, 7.31, 10.8, 14.9, 21.0, 22.7, 23.0, 26.6, 31.9, 37.7, 40.1, 43.3, 47.2, 58.6, 68.7, 73.0, 76.1, 76.2, 80.0, 81.0, 84.3, 128.3, 133.6, 133.8, 134.8, 136.1, 139.8, 163.0, 170.4, 206.0. m/z LCMS for $C_{45}H_{76}O_{10}SSi_3Na^+$: calcd: 915.4; found: 915.3.

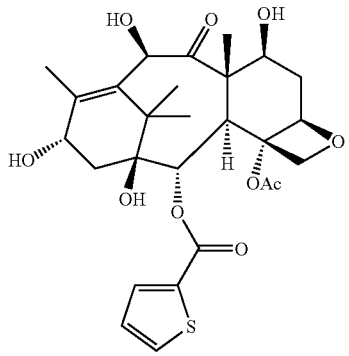

2-Debenzoyl-2-(2-thienoyl)-10-deacetyl-baccatin III

A solution of 7,10,13-tri(triethylsilyloxy)-2-debenzoyl-2-(2-thienoyl)baccatin III (6.38 g, 7.14 mmol) in anhydrous tetrahydrofuran (386 mL) was cooled to −30° C. Anhydrous pyridine (106 mL, 1.33 mol) was added to the solution and the reaction was kept at −30° C. in a dry ice and acetone bath. HF/Pyridine (106 mL) was added dropwise and the reaction was allowed to stir with gradual warming to room temperature overnight. The reaction was quenched with saturated aqueous sodium bicarbonate and extracted into ethyl acetate (2×50 mL). The combined organic layers were washed with water (50 mL), then brine (50 mL), and dried over sodium sulfate and concentrated in vacuo. The crude material was triturated with hexane and decanted, then used without further purification. $^1$H NMR (CDCl$_3$) δ 1.08 (s, 3 H), 1.10 (s, 3 H), 1.38 (d, J=8.0 Hz, 1 H), 1.75 (s, 3 H), 1.84 (m, 1 H), 1.99 (d, J=4.8 Hz, 1 H), 2.07 (s, 3 H), 2.61 (m, 1 H), 3.98 (d, J=7.2 Hz, 1 H), 4.16 (d, J=2.0 Hz, 1 H), 4.27 (m, 2 H), 4.44 (d, J=8.4 Hz, 1 H), 4.52 (m, 5 H), 4.87 (m, 1 H), 4.98 (d, J=7.6 Hz, 1 H), 5.24 (d, J=1.6 Hz, 1 H), 5.54 (d, J=7.2 Hz, 1 H), 7.15 (dd, J=4.0, 4.8 Hz, 1 H), 7.64 (dd, J=1.2, 5.2 Hz, 1 H), 7.87 (dd, J=1.2, 4.0 Hz, 1 H). $^{13}$C NMR (CDCl$_3$) δ 10.1, 15.4, 20.0, 22.9, 27.0, 37.5, 39.0, 42.9, 47.2, 58.0, 60.7, 68.3, 72.5, 75.4, 79.3, 81.0, 84.5, 128.4, 133.3, 134.0, 135.0, 135.2, 142.6, 162.9, 171.2, 212.1. m/z LCMS for $C_{27}H_{34}O_{10}SNa^+$: calcd: 573.2; found: 573.2.

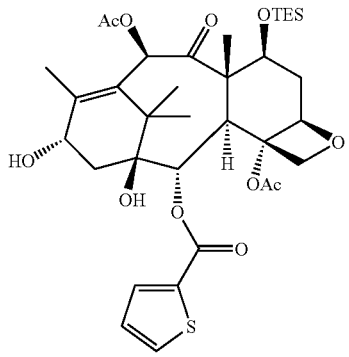

7-Triethylsilyloxy-2-debenzoyl-2-(2-thienoyl)baccatin III

To a mixture of 2-debenzoyl-2-(2-thienoyl)-10-deacetyl-baccatin III (3.93 g, 7.14 mmol) and imidazole (1.94 g, 28.5 mmol) in pyridine (266 ml) was added chlorotriethylsilane (2.14 g, 14.3 mmol) dropwise. The reaction was allowed to stir for 10 minutes at room temperature, after which it was observed by tlc to be complete. Acetic anhydride (13.5 mL, 143 mmol) was added dropwise to the mixture and the resulting mixture was stirred overnight at room temperature. The mixture was extracted into ethyl acetate (2×50 mL), and the combined organic layers were washed with water (50 mL), saturated aqueous sodium bicarbonate (50 mL), water (50 mL), then brine (50 mL). The organic layer was dried over anhydrous sodium sulfate and concentrated in vacuo. The crude material was purified over silica gel using 30% ethyl acetate in methylene chloride as the eluant. The fractions containing the desired product were pooled and concentrated to give 3.00 g of the title compound as a white solid. $^1$H NMR (CDCl$_3$) δ 0.58 (m, 6 H), 0.92 (t, J=8.0 Hz, 9 H), 1.04 (s, 3 H), 1.18 (s, 3 H), 1.68 (s, 3 H), 1.88 (m, 1 H), 1.99 (d, J=5.2 Hz, 1 H), 2.176 (s, 3 H), 2.182 (s, 3 H), 2.25 (m, 2 H), 2.26 (s, 3 H), 2.53 (m, 1 H), 3.84 (d, J=7.2 Hz, 1 H), 4.22 (d, J=8.4 Hz, 1 H), 4.43 (d, J=8.4 Hz, 1 H), 4.48 (dd, J=6.8, 10.4 Hz, 1 H), 4.83 (m, 1 H), 4.96 (d, J=8.4 Hz, 1 H), 5.54 (d, J=7.2 Hz, 1 H), 6.45 (s, 1 H), 7.14 (dd, J=3.6, 4.8 Hz, 1 H), 7.63 (dd, J=1.2, 5.2 Hz, 1 H), 7.87 (dd, J=1.2, 3.6 Hz, 1 H). $^{13}$C NMR (CDCl$_3$) δ 5.6, 7.1, 10.3, 15.3, 20.4, 21.3, 22.3, 27.2, 37.6, 38.6, 43.1, 47.5, 59.0, 68.3, 72.7, 75.4, 76.1, 79.2, 81.1, 84.6, 128.4, 133.0, 133.3, 133.9, 134.9, 144.2, 163.0, 169.7, 171.2, 202.4. m/z LCMS for $C_{35}H_{50}O_{11}SSiNa^+$: calcd: 729.3; found: 729.1.

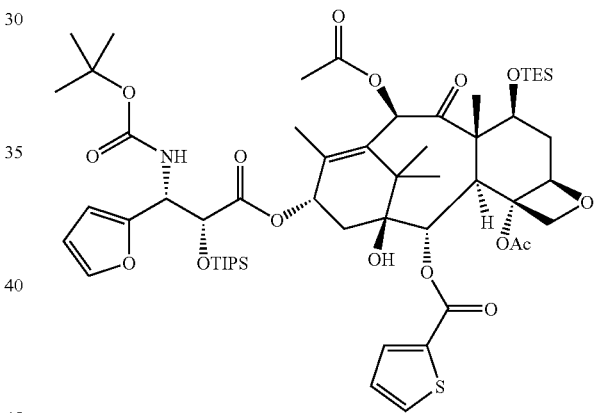

7-(triethylsilyloxy)-2'-(triisopropylsilyloxy)-3'-dephenyl-3'-(2-furyl)-2-debenzoyl-2-(2-thienoyl)-10-acetoxy-docetaxel To a well stirred solution of 7-triethylsilyloxy-2-debenzoyl-2-(2-thienoyl)baccatin III (370 mg, 0.523 mmol) and (3R,4S)-1-(tert-butoxy carbonyl)-3-triisopropylsilyloxy-4-(2-furyl)-2-azetidinone (300 mg, 0.732 mmol) in dry THF (37 mL) was added a solution of 1.0 M LiHMDS in THF (0.732 mL, 0.732 mmol) dropwise at −40° C., and the solution was stirred at −40° C. for 3 hours. The reaction was quenched with saturated aqueous ammonium chloride (10 mL), and the aqueous layer was extracted with ethyl acetate (15 ml×2). The combined organic extracts were dried over anhydrous magnesium sulfate and concentrated in vacuo. The crude material was purified over silica gel using 20% ethyl acetate in hexane as the eluant. The fractions containing the desired product were pooled and concentrated to give 572 g of the title compound as a white solid. $^1$H NMR (CDCl$_3$) δ 0.58 (m, 6 H), 0.96 (m, 30 H), 1.19 (s, 3 H), 1.21 (s, 3 H), 1.36 (s, 9 H), 1.58 (s, 3 H), 1.91 (m, 1 H), 2.03 (s, 3 H), 2.17 (s, 3 H), 2.32 (m, 2 H), 2.44 (s, 3 H), 2.53 (m, 1 H), 3.81 (d, J=6.8 Hz, 1 H), 4.25 (d, J=8.4 Hz, 1 H), 4.30 (d, J=8.4 Hz, 1 H), 4.47 (dd, J=6.4, 10.4 Hz, 1 H), 4.96 (m, 2 H), 5.26 (d, J=10.0 Hz, 1 H), 5.30 (d, J=10.0 Hz, 1 H), 5.59 (d, J=6.8 Hz, 1 H), 6.17 (t, J=9.2 Hz, 1 H), 6.24 (d, J=3.2 Hz, 1 H), 6.34 (dd, J=2.0, 3.2 Hz, 1 H), 6.47 (s, 1 H), 7.12 (dd, J=4.0, 4.8 Hz, 1 H), 7.36 (s, 1 H), 7.61 (dd, J=1.2, 4.8 Hz, 1 H), 7.88 (d, J=3.2 Hz, 1 H). $^{13}$C NMR (CDCl$_3$) δ 5.7, 7.1, 10.4, 12.8, 14.7, 18.1, 18.2, 21.2, 21.5, 23.2, 26.6, 28.5, 35.6, 37.6, 43.6, 47.0, 53.6, 58.8, 71.8, 72.6, 73.4, 75.4, 75.6, 77.6, 79.2, 80.6, 81.3, 84.6, 107.8, 111.1, 128.4, 133.2, 133.7, 134.1, 135.0, 141.1, 142.2, 152.4, 155.8, 162.9, 169.6, 170.6, 171.8, 202.2. m/z LCMS for $C_{56}H_{85}NO_{16}SSi_2Na^+$: calcd: 1138.5; found: 1138.4.

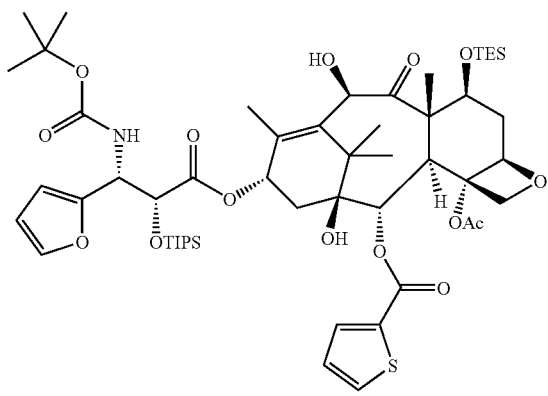

7-(triethylsilyloxy)-2'-(triisopropylsilyloxy)-3'-dephenyl-3'-(2-furyl)-2-debenzoyl-2-(2-thienoyl)-docetaxel To a solution of 7-(triethylsilyloxy)-2'-(triisopropylsilyloxy)-3'-dephenyl-3'-(2-furyl)-2-debenzoyl-2-(2-thienoyl)-10-acetoxy-docetaxel (555 mg, 0.497 mmol) in ethanol (15 mL) was added hydrazine monohydrate (5.82 mL) at room temperature. The reaction was stirred at rt and monitored by tlc. After 1.5 hours the reaction was completed by tlc and quenched with saturated aqueous ammonium chloride (10 mL). The aqueous layer was extracted with ethyl acetate (10 ml×2) and the combined organic extracts were dried over anhydrous sodium sulfate and concentrated in vacuo. The residue was purified by silica ptlc using a mixture of 50% ether, 40% hexane, and 10% ethyl acetate as the eluant to afford 310 mg of the title compound as a white solid. $^1$H NMR (CDCl$_3$) δ 0.54 (m, 6 H), 0.95 (m, 30 H), 1.08 (s, 3 H), 1.21 (s, 3 H), 1.35 (s, 9 H), 1.73 (s, 3 H), 1.92, (m, 1 H), 1.93 (s, 3 H), 2.26 (m, 2 H), 2.44 (s, 3 H), 2.47 (m, 1 H), 3.86 (d, J=7.2 Hz, 1 H), 4.24 (d, J=2.0 Hz, 1 H), 4.25 (d, J=8.4 Hz, 1 H), 4.38 (dd, J=6.4, 10.4 Hz, 1 H), 4.42 (d, J=8.4 Hz, 1 H), 4.94 (m, 2 H), 5.11 (d, J=2.0 Hz, 1 H), 5.28 (m, 2 H), 5.54 (d, J=7.2 Hz, 1 H), 6.23 (m, 2 H), 6.33 (dd, J=2.0, 3.2 Hz, 1 H), 7.11 (dd, J=4.0, 5.2 Hz, 1 H), 7.35 (d, J=0.8 Hz, 1 H), 7.59 (dd, J=1.2, 5.2 Hz, 1 H), 7.86 (d, J=3.2 Hz, 1 H). $^{13}$C NMR (CDCl$_3$) δ 5.5, 7.0, 10.4, 12.7, 14.7, 18.08, 18.09, 21.0, 23.1, 26.7, 28.5, 36.0, 37.6, 43.5, 46.8, 53.5, 58.1, 71.8, 73.2, 73.4, 74.5, 75.6, 77.0, 79.2, 80.5, 81.1, 84.6, 107.8, 111.1, 128.4, 133.2, 134.0, 134.9, 136.1, 138.9, 142.1, 152.4, 155.8, 162.8, 170.7, 171.6, 210.3. m/z LCMS for $C_{56}H_{85}NO_{16}SSi_2Na^+$: calcd: 1096.5; found: 1096.2.

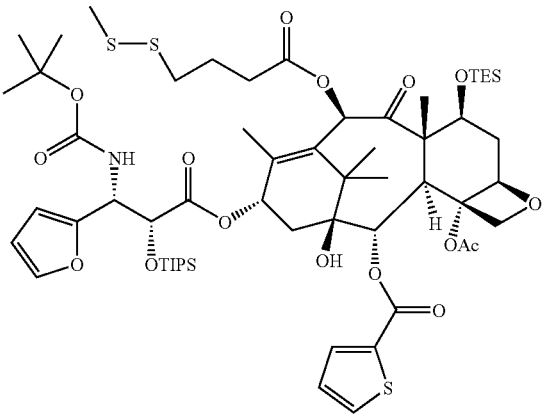

7-(triethylsilyloxy)-2'-(triisopropylsilyloxy)-3'-dephenyl-3'-(2-furyl)-2-debenzoyl-2-(2-thienyl)-10-(4-methyldithiobutanoyl)-docetaxel To a solution of 7-(triethylsilyloxy)-2'-(triisopropylsilyloxy)-3'-dephenyl-3'-(2-furyl)-2-debenzoyl-2-(2-thienoyl)-docetaxel (155 mg, 0.144 mmol) in methylene chloride (3.2 mL) was added DMAP (17.6 mg) and 4-methyldithio-butanoic acid (239 mg, 1.44 mmol). To this mixture was then added DIC (0.225 mL, 1.44 mmol) and the resulting mixture stirred overnight. Upon completion, the reaction was quenched with saturated aqueous ammonium chloride (10 mL) and extracted into methylene chloride (10 ml×2). The combined organic extracts were dried over anhydrous sodium sulfate and concentrated in vacuo. The residue was purified by silica ptlc using 20% ethyl acetate in hexane as the developing solvent to afford 158 mg of the title compound as a white solid. $^1$H NMR (CDCl$_3$) δ 0.57 (m, 6 H), 0.95 (m, 30 H), 1.17 (s, 3 H), 1.19 (s, 3 H), 1.35 (s, 9 H), 1.67 (s, 3 H), 1.88 (m, 1 H), 2.01 (s, 3 H), 2.11 (m, 2 H), 2.33 (m, 2 H), 2.39 (s, 3 H), 2.43 (s, 3 H), 2.51 (m, 1 H), 2.64 (m, 2 H), 2.82 (m, 2 H), 3.80 (d, J=7.2 Hz, 1 H), 4.24 (d, J=8.4 Hz, 1 H), 4.38 (d, J=8.4 Hz, 1 H), 4.46 (dd, J=6.4, 10.4 Hz, 1 H), 4.94 (d, J=8.4 Hz, 1 H), 4.97 (s, 1 H), 5.25 (d, J=10.4 Hz, 1 H), 5.29 (d, J=10.4 Hz, 1 H), 5.58 (d, J=7.2 Hz, 1 H), 6.15 (t, J=9.2 Hz, 1 H), 6.23 (d, J=3.2 Hz, 1 H), 6.33 (dd, J=2.0, 3.2 Hz, 1 H), 6.48 (s, 1 H), 7.11 (dd, J=4.0, 5.2 Hz, 1 H), 7.35 (d, J=1.2 Hz, 1 H), 7.60 (dd, J=1.2, 5.2 Hz, 1 H), 7.86 (d, J=3.2 Hz, 1 H). $^{13}$C NMR (CDCl$_3$) δ 5.7, 7.1, 10.4, 12.7, 14.7, 18.1, 22.9, 23.1, 23.4, 23.6, 24.6, 26.6, 28.5, 32.9, 35.6, 37.2, 43.5, 47.0, 53.6, 58.8, 71.8, 72.6, 73.4, 75.3, 75.5, 77.0, 79.1, 80.5, 81.2, 84.5, 107.8, 111.1, 128.4, 133.2, 133.6, 134.0, 135.0, 141.0, 142.2, 152.3, 155.8, 162.8, 170.6, 171.4, 171.8, 202.1. m/z LCMS for $C_{59}H_{91}NO_{16}S_3Si_2Na^+$: calcd: 1244.5; found: 1244.3.

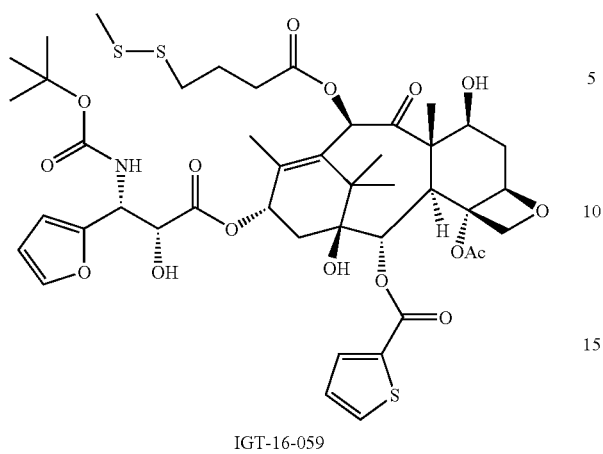

IGT-16-059

3'-dephenyl-3'-(2-furyl)-2-debenzoyl-2-(2-thienyl)-10-(4-methyldithio-butanoyl)-docetaxel To a solution of 7-(triethylsilyloxy)-2'-(triisopropylsilyloxy)-3'-dephenyl-3'-(2-furyl)-2-debenzoyl-2-(2-thienyl)-10-(4-methyldithiobutanoyl)-docetaxel (158 mg, 0.129 mmol) in pyridine-acetonitrile (1/1, 3.16 mL) was added HF/pyridine (70:30, 1.58 mL) at 0° C. The resulting mixture was stirred for 24 hours with gradual warming to room temperature. The reaction was quenched with saturated aqueous sodium bicarbonate (10 mL) and then extracted with ethyl acetate (2×20 mL). The combined organic layers were washed with water (15 mL) and brine (15 mL), dried over anhydrous sodium sulfate and concentrated in vacuo. The residue was purified by silica ptlc using 60% ethyl acetate in hexane as the developing solvent to afford 57.3 mg of the title compound as a white solid. $^1$H NMR (CDCl$_3$) δ 1.11 (s, 3 H), 1.24 (s, 3 H), 1.36 (s, 9 H), 1.66 (s, 3 H), 1.87 (s, 3 H), 2.14 (p, J=7.2 Hz, 2 H), 2.32 (d, J=9.2 Hz, 2 H), 2.37 (s, 3 H), 2.41 (s, 3 H), 2.51 (m, 1 H), 2.64 (m, 2 H), 2.82 (m, 2 H), 3.40 (bs, 1 H), 3.77 (d, J=7.2 Hz, 1 H), 4.23 (d, J=8.4 Hz, 1 H), 4.42 (d, J=8.4 Hz, 1 H), 4.40 (m, 1 H), 4.70 (s, 1 H), 4.96 (d, J=8.4 Hz, 1 H), 5.30 (m, 2H), 5.55 (d, J=7.2 Hz, 1 H), 6.20 (t, J=9.2 Hz, 1 H), 6.31 (m, 2 H), 6.36 (dd, J=2.0, 3.2 Hz, 1 H), 7.13 (dd, J=4.0, 4.8 Hz, 1 H), 7.40 (d, J=1.2 Hz, 1 H), 7.63 (dd, J=0.8, 4.8 Hz 1 H), 7.88 (d, J=3.2 Hz, 1 H). $^{13}$C NMR (CDCl$_3$) δ 9.9, 15.2, 22.2, 22.8, 23.5, 24.5, 27.0, 28.5, 32.9, 35.7, 35.9, 37.1, 43.4, 45.9, 52.1, 58.9, 72.1, 72.5, 72.8, 75.6, 75.9, 76.8, 79.4, 80.8, 81.2, 84.7, 107.8, 111.0, 128.5, 133.0, 133.2, 134.2, 135.1, 142.7, 142.8, 151.6, 155.5, 162.8, 170.6, 173.0, 173.5, 203.9. m/z LCMS for C$_{44}$H$_{57}$NO$_{16}$S$_3$Na$^+$: calcd: 974.3; found: 974.1.

Synthesis of 3'-dephenyl-3'-(2-furyl)-2-debenzoyl-2-(2-furoyl)-10-(4,4-dimethyl-4-methyldithiobutanoyl)-docetaxel

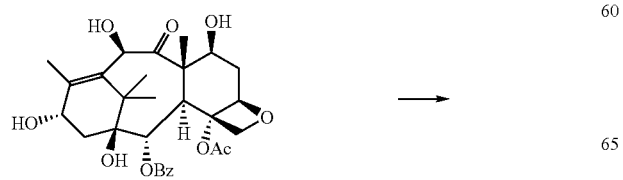

-continued

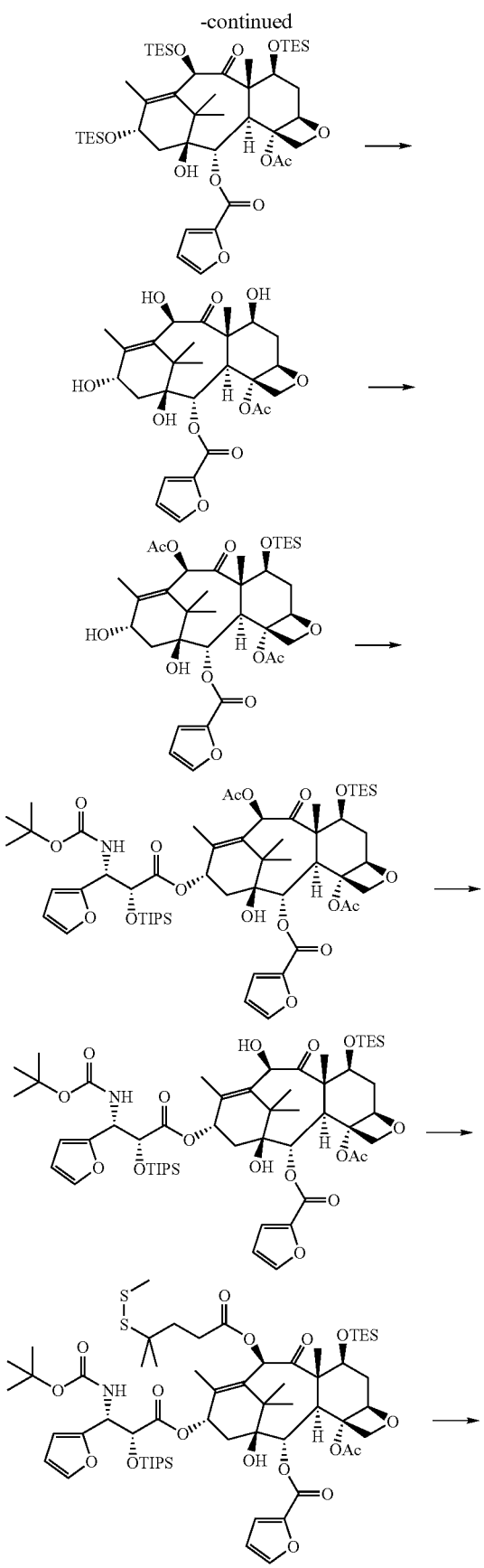

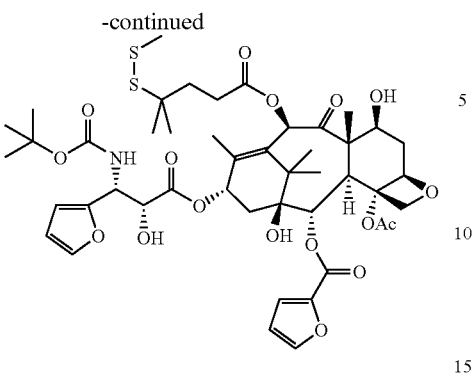

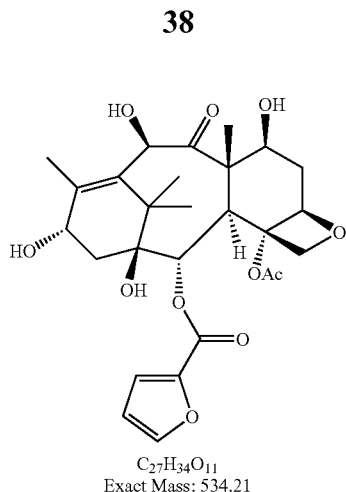

C₂₇H₃₄O₁₁
Exact Mass: 534.21

2-debenzoyl-2-(2-furoyl)-10-deacetyl baccatin III

A solution of 7,10,13-(triethylsilyloxy)-2-debenzoyl-2-(2-furoyl)-10-deacetyl baccatin III (5.9 g, 6.74 mmol) in anhydrous tetrahydrofuran (360 mL) was cooled to −30 C in a dry ice/acetone bath. Anhydrous pyridine (88 mL) was added to the solution and the reaction was kept at −30 C in a dry ice and acetone bath. HF/Pyridine (60%, 88 mL) was added drop wise and the reaction was allowed to stir with gradual warming to room temperature overnight. The reaction was then quenched with saturated aqueous sodium bicarbonate and extracted into ethyl acetate (2×100 mL). The combined organic layers were washed with water (100 mL), then brine (100 mL), dried over anhydrous sodium sulfate and concentrated in vacuo. The crude material was triturated with hexane and decanted then used in the next step without further purification. m/z LC/MS for $C_{27}H_{34}O_{11}Na^+$: calcd: 557.2; found: 557.2.

C₄₅H₇₆O₁₁Si₃
Exact Mass: 876.47

7,10,13-(triethylsilyloxy)-2-debenzoyl-2-(2-furoyl)-10-deacetyl baccatin III

To a flask containing a solution of 7,10,13-(triethylsilyloxy)-2-debenzoyl-10-deacetyl baccatin III (4.19 g, 5.35 mmol) in methylene chloride (65 mL) was added DMAP (3.95 g, 6 eq), 2-furoic acid (6.01 g, 10 eq), and DIC (8.4 mL, 10 eq). The reaction was allowed to stir at room temperature for 4 hours, after which it was complete by tlc. The product was extracted into ethyl acetate, washed with water, saturated aqueous sodium bicarbonate, water, and brine. The combined organic layers were dried over anhydrous sodium sulfate and concentrated in vacuo. The crude material was purified over silica gel (gradient elution of 10 to 20% ethyl acetate in hexanes) to give the desired product as a white solid. ¹H NMR (CDCl₃) δ 0.61 (m, 18H), 0.94 (m, 27H), 1.14 (s, 3H), 1.17 (s, 3H), 1.60 (s, 3H), 1.84 (m, 1H), 1.93 (s, 3H), 2.07 (m, 2H), 2.20 (s, 3H), 2.48 (m, 1H), 3.77 (d, J=7.2 Hz, 1H), 4.13 (d, J=8.4 Hz, 1H), 4.33 (d, J=8.4 Hz, 1H), 4.37 (dd, J=6.8, 10.8 Hz, 1H), 4.90 (m, 2H), 5.15 (s, 1H), 5.48 (d, J=7.2 Hz, 1H), 6.50 (dd, J=1.6, 3.2 Hz, 1H), 7.15 (t, J=3.2 Hz, 1H), 7.58 (d, J=1.6 Hz, 1H). m/z LC/MS for $C_{45}H_{76}O_1Si_3Na^+$: calcd: 899.5; found: 899.3.

C₃₅H₅₀O₁₂Si
Exact Mass: 690.31

7-Triethylsilyloxy-2-debenzoyl-2-(2-furoyl)-baccatin III

To a mixture of 2-debenzoyl-2-(2-furoyl)-10-deacetyl baccatin III (3.10 g, 5.8 mmol) and imidazole (2.73 g, 6 eq) in pyridine (25 ml) was added chlorotriethylsilane (1.95 g, 2 eq) dropwise. The reaction was allowed to stir for 10 min at room temperature, after which it was observed by tlc to be complete. Acetic anhydride (11 mL, 20 eq) was added dropwise to the mixture and the resulting mixture was stirred overnight at room temperature. The mixture was extracted into ethyl acetate (2×50 mL), and the combined organic layers were washed with water (100 mL), saturated aqueous sodium bicarbonate (100 mL), water (50 mL), then brine (50 mL). The organic layer was dried over anhydrous sodium sulfate and concentrated in vacuo. The crude material was purified over silica gel using 20% ethyl acetate in methylene chloride as the eluant. The fractions containing the desired product were pooled and concentrated to give 2.075 g of the title compound as a white solid. $^1$H NMR (CDCl$_3$) δ 0.57 (m, 6H), 0.91 (m, 9H), 1.02 (s, 3H), 1.15 (s, 3H), 1.65 (s, 3H), 1.69 (s, 1H), 1.85 (m, 1H), 2.16 (s, 6H), 2.20 (m, 1H), 2.22 (s, 3H), 2.25 (m, 1H), 2.52 (m, 1H), 3.82 (d, J=7.2 Hz, 1H), 4.15 (d, J=8.4 Hz, 1H), 4.37 (d, J=8.4 Hz, 1H), 4.46 (dd, J=6.8, 10.4 Hz, 1H), 4.80 (m, 1H), 4.95 (d, J=8.4 Hz, 1H), 5.51 (d, J=7.2 Hz, 1H), 6.43 (s, 1H), 6.53 (dd, J=1.6, 3.2 Hz, 1H), 7.22 (d, J=3.2 Hz, 1H), 7.62 (s, 1H). m/z LC/MS for C$_{35}$H$_{50}$O$_{12}$SiNa$^+$: calcd: 713.3; found: 713.3.

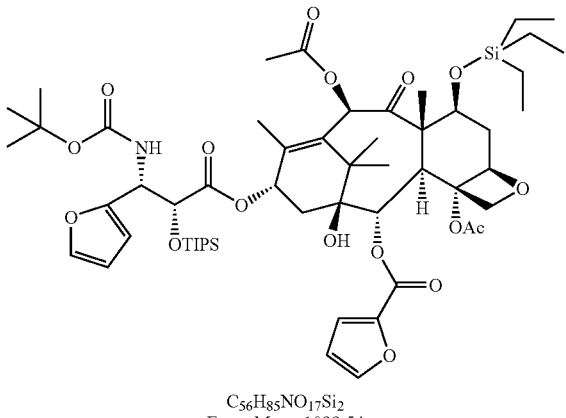

C$_{56}$H$_{85}$NO$_{17}$Si$_2$
Exact Mass: 1099.54

7-(triethylsilyloxy)-2'-(triisopropylsilyloxy)-3'-dephenyl-3'-(2-furyl)-2-debenzoyl-2-(2-furoyl)-10-acetoxy-docetaxel To a well stirred solution of 7-Triethylsilyloxy-2-debenzoyl-2-(2-furoyl)-baccatin III (2.68 g, 3.88 mmol) and (3R, 4S)-1-(tert-butoxy carbonyl)-3-triisopropylsilyloxy-4-(2-furyl)-2-azetidinone (2.22 g, 5.43 mmol) in dry THF (25 mL) was added a solution of 1.0 M LiHMDS in THF (5.43 mL, 5.43 mmol) dropwise at −40° C., and the solution was stirred at −40° C. for 3 hours. The reaction was quenched with saturated aqueous ammonium chloride (25 mL), and the aqueous layer was extracted with ethyl acetate (25 ml×3). The combined organic extracts were washed with water (25 mL), brine (25 mL), dried over anhydrous sodium sulfate and concentrated in vacuo. The residue was purified by silica gel column using 20% ethyl acetate in hexane as the eluant to afford 4.27 g (93%) of the title compound as a white solid. $^1$H NMR (CDCl$_3$) δ 0.58 (m, 6H), 0.92 (m, 9H), 1.00 (m, 21H), 1.16 (s, 3H), 1.18 (s, 3H), 1.40 (s, 9H), 1.65 (s, 3H), 1.90 (m, 1H), 2.02 (s, 3H), 2.17 (s, 3H), 2.23 (m, 2H), 2.42 (s, 3H), 2.53 (m, 1H), 3.81 (d, J=7.2 Hz, 1H), 4.21 (d, J=8.4 Hz, 1H), 4.39 (d, J=8.4 Hz, 1H), 4.47 (dd, J=6.4, 10.8 Hz, 1H), 4.94 (d, J=8.0 Hz, 1H), 4.97 (s, 1H), 5.57 (m, 2H), 5.58 (d, J=7.2 Hz, 1H), 6.18 (t, J=8.8 Hz, 1H), 6.23 (d, J=3.2 Hz, 1H), 6.33 (dd, J=1.6, 3.2 Hz, 1H), 6.46 (s, 1H), 6.48 (dd, J=1.6, 3.2 Hz, 1H), 7.31 (d, J=3.2 Hz, 1H), 7.35 (d, J=0.8 Hz, 1H), 7.62 (s, 1H). m/z LC/MS for C$_{56}$H$_{85}$NO$_{17}$Si$_2$Na$^+$: calcd: 1122.5; found: 1122.3.

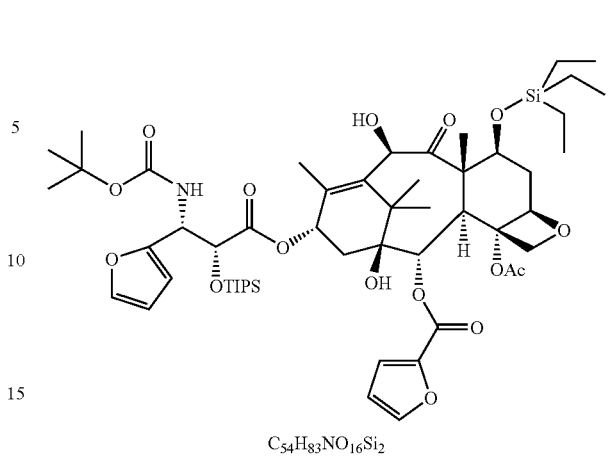

C$_{54}$H$_{83}$NO$_{16}$Si$_2$
Exact Mass: 1057.53

7-(triethylsilyloxy)-2'-(triisopropylsilyloxy)-3'-dephenyl-3'-(2-furyl)-2-debenzoyl-2-(2-furoyl)-docetaxel Hydrazine monohydrate (4.25 mL) was added dropwise to a solution of 7-(triethylsilyloxy)-2'-(triisopropylsilyloxy)-3'-dephenyl-3'-(2-furyl)-2-debenzoyl-2-(2-furoyl)-10-acetoxy-docetaxel (400 mg, 0.363 mmol) in ethanol (11 mL). The reaction was allowed to stir at room temperature for 30 minutes after which it was complete and quenched with saturated aqueous ammonium chloride. The product was extracted with ethyl acetate, washed with water and brine, dried over sodium sulfate and concentrated in vacuo. The crude material was purified by silica gel PTLC using 50% ether, 40% hexanes, and 10% ethyl acetate as the mobile phase to give the desired product as a white solid. $^1$H NMR (CDCl$_3$) δ 0.58 (m, 6H), 0.92 (m, 9H), 1.00 (m, 21H), 1.08 (s, 3H), 1.22 (s, 3H), 1.37 (s, 9H), 1.73 (s, 3H), 1.89 (m, 1H), 1.93 (s, 3H), 2.23 (m, 2H), 2.42 (s, 3H), 2.53 (m, 1H), 3.87 (d, J=7.2 Hz, 1H), 4.23 (m, 2H), 4.39 (m, 2H), 4.95 (m, 2H), 5.11 (s, 1H), 5.28 (m, 2H), 5.54 (d, J=7.2 Hz, 1H), 6.23 (m, 2H), 6.33 (dd, J=1.6, 3.2 Hz, 1H), 6.52 (dd, J=1.6, 3.6 Hz, 1H), 7.31 (d, J=3.6 Hz, 1H), 7.35 (d, J=0.8 Hz, 1H), 7.62 (s, 1H). m/z LC/MS for C$_{54}$H$_{83}$NO$_{16}$Si$_2$Na$^+$: calcd: 1080.5; found: 1080.7.

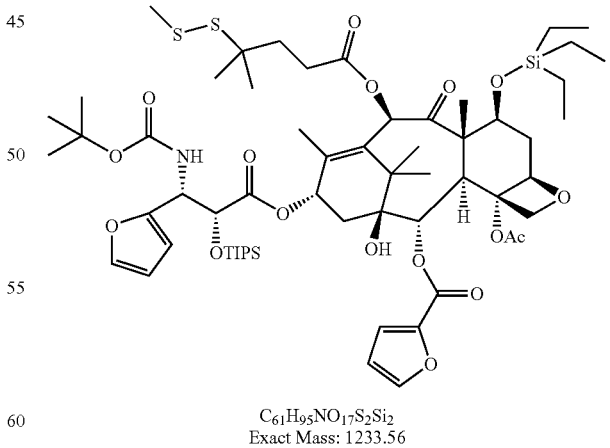

C$_{61}$H$_{95}$NO$_{17}$S$_2$Si$_2$
Exact Mass: 1233.56

7-(triethylsilyloxy)-2'-(triisopropylsilyloxy)-3'-dephenyl-3'-(2-furyl)-2-debenzoyl-2-(2-furoyl)-10-(4,4-dimethyl-4-methyldithiobutanoyl)-docetaxel To a flask containing a solution of 7-(triethylsilyloxy)-2'-(triisopropylsilyloxy)-3'-dephenyl-3'-(2-furyl)-2-debenzoyl- 2-(2-furoyl)-docetaxel (69.9 mg, 0.066 mmol) in methylene chloride (1.5 mL) was added DMAP (1 eq), 4,4-dimethyl-4-methyldithiobutanoic acid (10 eq), and DIC (10 eq). The reaction was allowed to stir at room temperature overnight, after which it was complete and quenched with saturated aqueous ammonium chloride. The mixture was diluted with methylene chloride (10 mL), washed with water (20 mL), dried over sodium sulfate and concentrated in vacuo. The crude material was purified by silica gel PTLC using 30% ethyl acetate in hexane as the eluant to give 74 mg of product (65%). $^1$H NMR (CDCl$_3$) δ 0.58 (m, 6H), 0.92 (m, 9H), 1.00 (m, 21H), 1.18 (s, 3H), 1.20 (s, 3H), 1.29 (s, 6H), 1.36 (s, 9H), 1.67 (s, 3H), 1.89 (m, 1H), 1.98 (t, J=8.8 Hz, 2H), 2.00 (s, 3H), 2.23 (m, 2H), 2.40 (s, 3H), 2.42 (s, 3H), 2.53 (m, 3H), 3.81 (d, J=7.2 Hz, 1H), 4.21 (d, J=8.0 Hz, 1H), 4.39 (d, J=8.0 Hz, 1H), 4.47 (dd, J=6.4, 10.8 Hz, 1H), 4.94 (d, J=8.4 Hz, 1H), 4.97 (s, 1H), 5.28 (m, 2H), 5.57 (d, J=7.2 Hz, 1H), 6.17 (t, J=8.8 Hz, 1H), 6.23 (d, J=3.2 Hz, 1H), 6.33 (dd, J=2.0, 3.2 Hz, 1H), 6.47 (s, 1H), 6.52 (dd, J=1.6, 3.6 Hz, 1H), 7.31 (d, J=3.2 Hz, 1H), 7.35 (s, 1H), 7.62 (s, 1H). m/z LC/MS for C$_{61}$H$_{95}$NO$_{17}$S$_2$Si$_2$Na$^+$: calcd: 1256.5; found: 1256.6

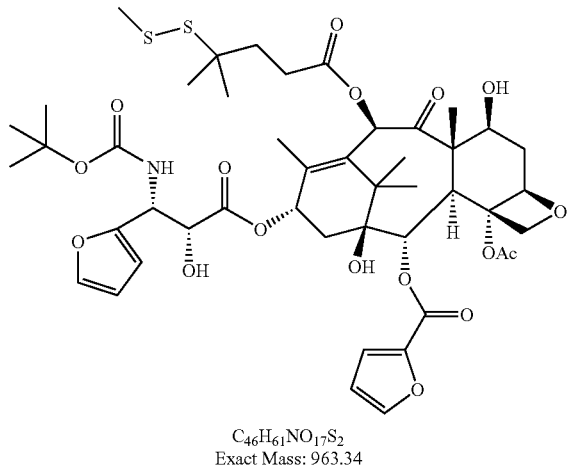

C$_{46}$H$_{61}$NO$_{17}$S$_2$
Exact Mass: 963.34

3'-dephenyl-3'-(2-furyl)-2-debenzoyl-2-(2-furoyl)-10-(4,4-dimethyl-4-methyldithiobutanoyl)-docetaxel Hydrogen fluoride/pyridine (0.57 mL) was added dropwise at 0° C. to a solution of 7-(triethylsilyloxy)-2'-(triisopropylsilyloxy)-3'-dephenyl-3'-(2-furyl)-2-debenzoyl-2-(2-furoyl)-10-(4,4-dimethyl-4-methyldithiobutanoyl)-docetaxel (56.9 mg, 0.0461 mmol) in a solution of 1:1 pyridine/acetonitrile (2.28 mL). The reaction was allowed to stir with gradual warming to room temperature overnight after which it was complete by tlc. The reaction was quenched with saturated aqueous sodium bicarbonate and the product was extracted with ethyl acetate, washed with water then brine, dried over anhydrous sodium sulfate and concentrated in vacuo. The crude material was purified by silica gel PTLC using 70% ethyl acetate in hexanes as the eluant to give 35.7 mg (80.4%) of pure product as a white solid. $^1$H NMR (CDCl$_3$) δ 1.12 (s, 3H), 1.20 (s, 3H), 1.32 (s, 6H), 1.38 (s, 9H), 1.67 (s, 3H), 1.85 (m, 2H), 1.98 (m, 2H), 2.00 (m, 3H), 2.31 (m, 1H), 2.36 (s, 3H), 2.44 (s, 3H), 2.53 (m, 3H), 3.34 (d, J=5.6, 1H), 3.78 (d, J=7.2 Hz, 1H), 4.15 (d, J=7.2 Hz, 1H), 4.41 (m, 2H), 4.71 (dd, J=1.6, 5.6 Hz, 1H), 4.95 (d, J=8.0 Hz, 1H), 5.29 (m, 2H), 5.56 (d, J=6.8 Hz, 1H), 6.21 (t, J=8.8 Hz, 1H), 6.29 (s, 1H), 6.31 (d, J=3.2 Hz, 1H), 6.36 (dd, J=1.6, 3.2 Hz, 1H), 6.54 (dd, J=1.6, 3.6 Hz, 1H), 7.31 (d, J=3.2 Hz, 1H), 7.39 (s, 1H), 7.62 (s, 1H). /z LC/MS for C$_{46}$H$_{61}$NO$_{17}$S$_2$Na$^+$: calcd: 986.3; found: 986.4.

The activity of the compounds of the present invention were determined following the proceeding described by Riou, Naudin and Lavelle in Biochemical and Biophysical Research Communications; Vol. 187, No 1, 1992, p 164-170.

| C2 Heterocycle disulfides | | A549 | MCF7 |
|---|---|---|---|
| | IGT-17-020 | >1.0 | >1.0 |

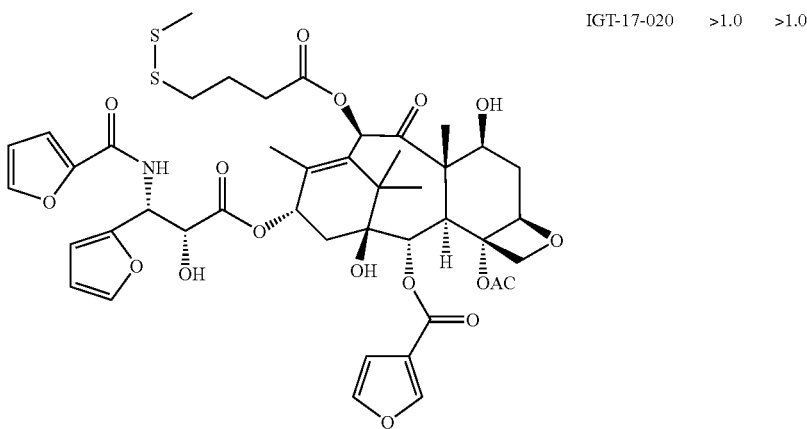

-continued
| C2 Heterocycle | | A549 | MCF7 |
|---|---|---|---|
| 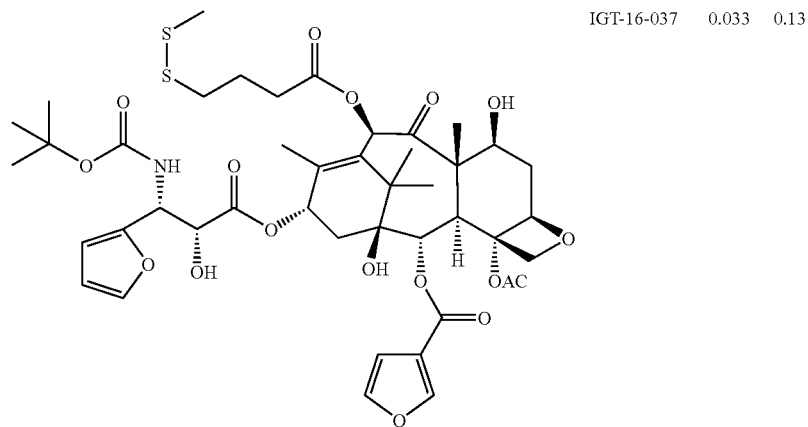 | IGT-16-037 | 0.033 | 0.13 |
| 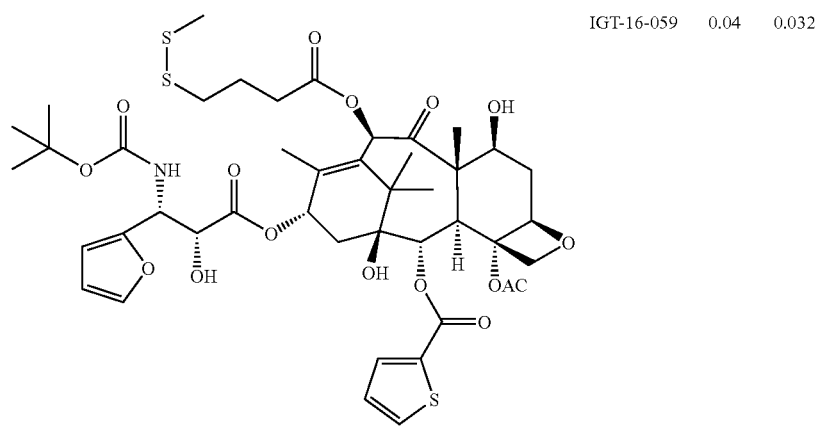 | IGT-16-059 | 0.04 | 0.032 |
| 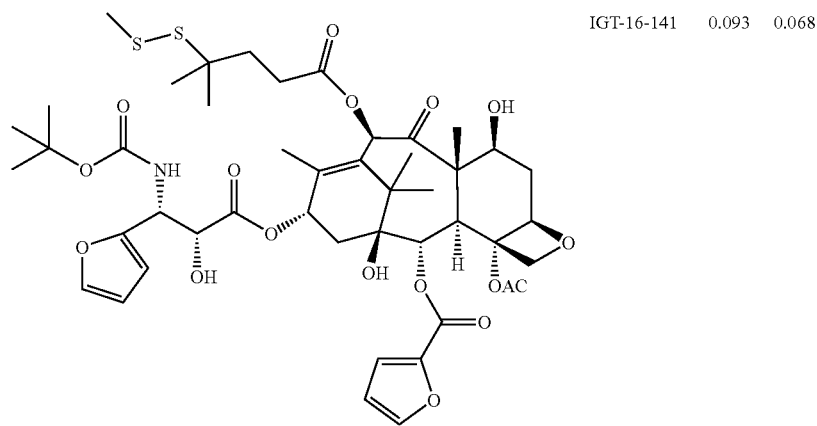 | IGT-16-141 | 0.093 | 0.068 |

| C2 Heterocycle | A549 | MCF7 |
|---|---|---|

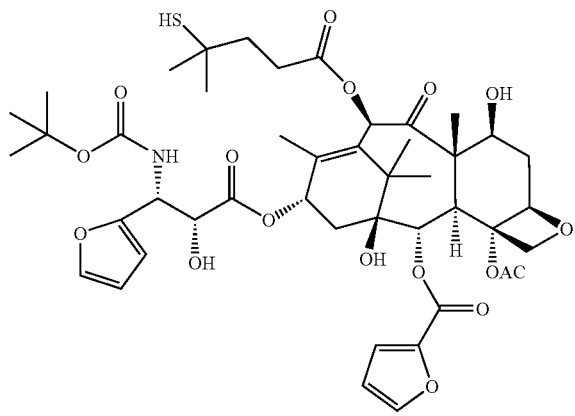

C₄₅H₅₉NO₁₇S
Exact Mass: 917.35
IGT-16-141-SH

3'-dephenyl-3'-(2-furyl)-2-debenzoyl-2-(2-furoyl)-10-(4,4-dimethyl-4-sulfhydryl-butanoyl)-docetaxel In a small vial dissolved 3'-dephenyl-3'-(2-furyl)-2-debenzoyl-2-(2-furoyl)-10-(4,4-dimethyl-4-methyldithiobutanoyl)-docetaxel (34 mg, 0.0343 mmol) in a mixture of methanol (0.96 mL) and ethyl acetate (0.69 mL). In a separate vial dissolved DTT (55 mg, 0.343 mmol) in KP buffer pH 7.5 (0.96 mL) which was then added to the taxoid solution. The reaction was monitored by hplc until it was found to be complete (~16 hr). The reaction was quenched with KP buffer pH 6.5 (6 mL) and extracted with ethyl acetate (3×20 mL). The combined organic layers were washed with water, dried over anhydrous sodium sulfate, and concentrated. The residue was purified by hplc using a diol column to give the desired product (21.5 mg, 64%) which was immediately aliquoted and stored for use in conjugation. m/z LC/MS for $C_{45}H_{59}NO_{17}SNa^+$: calcd: 940.4; found: 940.4.

Conjugates of the taxanes of the invention and a cell binding agent can be formed using any techniques presently known or later developed. Numerous methods of conjugation are taught in U.S. Pat. Nos. 5,416,064 and 5,475,092. The taxane ester can be modified to yield a free amino group and then linked to an antibody or other cell binding agent via an acid labile linker or a photolabile linker. The taxane ester can be condensed with a peptide and subsequently linked to a cell binding agent to produce a peptidase labile linker The hydroxyll group on the taxane ester can be succinylated and linked to a cell binding agent to produce a conjugate that can be cleaved by intracellular esterases to liberate free drug. Most preferably, the taxane ethers, esters, or carbamates are treated to create a free or protected thiol group, and then the disulfide- or thiol-containing taxanes are linked to the cell binding agent via disulfide bonds.

Representative conjugates of the invention are antibody-taxane, antibody fragment-taxane epidermal growth factor (EGF)-taxane, melanocyte stimulating hormone (MSH)-taxane, thyroid stimulating hormone (TSH)-taxane, estrogen-taxane, estrogen analogue-taxane, androgen-taxane, androgen analogue-taxane, and folate-taxane.

Taxane conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio)butyrate (SDPB), N-sulfosuccinimidyl-3-(2-(5-nitro-pyridyldithio)butyrate (SSNPB), 2-iminothiolane, or S-acetylsuccinic anhydride by known methods. See, Carlsson et al, 173 Biochem. J. 723-737 (1978); Widdison et al., U.S. Pat. No. 6,913,748; Blattler et al, 24 Biochem. 1517-1524 (1985); Lambert et al, 22 Biochem. 3913-3920 (1983); Klotz et al, 96 Arch. Biochem. Biophys. 605 (1962); and Liu et al, 18 Biochem. 690 (1979), Blakey and Thorpe, 1 Antibody, Immunoconjugates & Radiopharmaceuticals, 1-16 (1988), Worrell et al 1 Anti-Cancer Drug Design 179-184 (1986). The free or protected thiol-containing cell binding agent thus derived is then reacted with a disulfide- or thiol-containing taxane to produce conjugates. The conjugates can be purified by HPLC or by gel filtration.

Preferably monoclonal antibody- or cell binding agent-taxane conjugates are those that are joined via a disulfide bond, as discussed above, that are capable of delivering taxane molecules. Such cell binding conjugates are prepared by known methods such as by modifying monoclonal antibodies with succinimidyl pyridyl-dithiopropionate (SPDP) (Carlsson et al, 173 Biochem. J. 723-737 (1978)). The resulting thiopyridyl group is then displaced by treatment with thiol-containing taxanes to produce disulfide linked conjugates. Alternatively, in the case of the aryldithio-taxanes, the formation of the cell binding conjugate is effected by direct displacement of the aryl-thiol of the taxane by sulfhydryl groups previously introduced into antibody molecules. Conjugates containing 1 to 10 taxane drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing taxane (1.3 molar eq./dithiopyridyl group). The release of thio-nitropyridine from the modified antibody is monitored spectrophotometrically at 325 nm and is complete in about 16 hours. The antibody-taxane conjugate is purified and freed of unreacted drug and other low molecular weight material by gel filtration through a column of Sephadex G-25 or Sephacryl S300. The number of taxane moieties bound per antibody molecule can be determined by measuring the ratio of the absorbance at 230 nm and 275 nm. An average of 1-10 taxane molecules/antibody molecule can be linked via disulfide bonds by this method.

The effect of conjugation on binding affinity towards the antiogen-expreesing cells can eb determined using the methods previously described by Liu et al., 93 Proc. Natl. Acad. Sci 8618-8623 (1996). Cytotoxicity of the taxanes and their antibody conjugates to non-adherent cell lines such as Namalwa and HL-60 can be measured by back-extrapolation of cell proliferation curves as described in Goldmacher et al, 135 *J. Immunol.* 3648-3651 (1985). Cytotoxicity of these compounds to adherent cell lines such as COLO 205 and A-375 can be determined by clonogenic assays as described in Goldmacher et al, 102 *J. Cell Biol.* 1312-1319 (1986).

EXAMPLES

Conjugation of taxoids to monoclonal antibodies. HuC242 antibody that binds to the CanAg antigen preferentially expressed on the surface of human colon tumor cells and on other solid tumors was selected for conjugation of taxoids.

In the first step, the antibody was reacted with the modifying agent N-sulfosuccinimidyl 5-nitro-2-pyridyldithiobutanoate (SSNPB) to introduce nitropyridyldithio groups. A solution of huC242 antibody (15.0 mg, 0.10 μmol) at a concentration of 8 mg/mL in an aqueous buffer containing 0.05 M potassium phosphate, 0.05 M sodium chloride and 2 mM ethylenediaminetetra-acetic acid (EDTA), pH 6.5 (1.90 mL) was treated with a 7.5-fold molar excess of a solution of SSNPB (0.75 μmol, 0.35 mg) in dimethylacetamide (DMA) (0.1 mL). The reaction mixture was stirred at room temperature for 90 min. and then loaded on to a Sephadex G25 gel filtration column that had been previously equilibrated into an aqueous buffer containing 0.05 M potassium phosphate, 0.05 M sodium chloride and 2 mM EDTA, pH 7.5. The modified antibody-containing fractions were collected and pooled to yield 13.4 mg (89%) of product. A small aliquot of the modified antibody was treated with dithiothreitol to cleave the nitro-pyridyl disulfide and the released nitro-pyridine-2-thione was assayed spectrophotometrically ($\epsilon_{325nm}$=10,964 $M^{-1}cm^{-1}$ and $\epsilon_{280nm}$=3,344 $M^{-1}cm^{-1}$ for nitro-pyridine-2-thione, and $\epsilon_{280nm}$=217,560 $M^{-1}cm^{-1}$ for the antibody. An average of 5.7 nitro-pyridyldisulfide molecules were linked per molecule of antibody.

The modified antibody (13.3 mg, 0.09 μmol) was diluted to 2.5 mg/mL in the above buffer at pH 7.5 and then treated with a solution of the taxoid IGT-16-141-SH (0.82 μmol, 0.75 mg) in DMA, such that the final concentration of DMA in the buffer was 20%. The conjugation mixture was stirred at room temperature for 16 h. The reaction mixture was purified by passage through a Sephadex G25 gel filtration column, that had been previously equilibrated in a phosphate-buffered saline (PBS) buffer at pH 6.5. Fractions containing monomeric antibody-taxoid conjugate were pooled and dialyzed into the PBS buffer. The final conjugate (9.4 mg) was assayed spectrophotometrically using the following extinction coefficients: ($\epsilon_{252nm}$=16,415 $M^{-1}cm^{-1}$, $\epsilon_{280nm}$=566 $M^{-1}cm^{-1}$ for the taxoid, and $\epsilon_{280nm}$=217,560 $M^{-1}cm^{-1}$ for the antibody. The conjugate contained, on the average, 3.54 taxoids linked per molecule of antibody.

Binding Assay. The relative binding affinities of the huC242 antibody and its taxoid conjugate on antigen-expressing HT-29 human colon tumor cells was determined using a fluorescence-based assay. The antibody-taxoid conjugate and naked antibody at starting concentrations of 1 a $10^{-7}$ M were added to 96-well round bottom plates and titrated using 3-fold serial dilutions so that there are duplicates for each concentration. HT-29 cells, were added at 50,000 cells per well to each well containing various concentrations of the antibody or conjugate, as well as to control wells. The plates were incubated on ice for 3 hours. After the incubation period, the cells in the plate were washed, and a fluorescence labeled secondary antibody that binds to a humanized IgG, like huC242, was added, and the plates were incubated for 1 hour on ice. The plates were washed again after the incubation period, and the cells are fixed with 1% formaldehyde/PBS solution. The fluorescence in each well of the plates was read using a Becton Dickinson FACSCalibur fluorescence analyzer. Data are plotted as a percent of the maximum fluorescence obtained at the highest concentration of antibody or conjugate (FIG. 1).

The results demonstrate that conjugation of taxoids to antibodies does not significantly alter the binding affinity to target cells.

In vitro potency and specificity of huC242-Taxoid conjugate. Samples of free taxoid or huC242-Taxoid conjugate were added to a 96-well flat bottomed tissue culture plate and titrated using serial dilutions ranging from $1 \times 10^{-12}$ M to $3 \times 10^{-7}$ M. Human colon tumor cells, COLO 205, or human melanoma cells, A-375, were added to the wells in such a way that there were triplicate samples for each drug concentration for each cell line. The plates were incubated at 37° C. in an atmosphere of 5% $CO_2$ for 4 days.

At the end of the incubation period, 20 μl of the tetrazolium reagent WST-8 (2-(2-methoxy-nitrophenyl)-3-(4-nitrophenyl)-5-(2,4-disulfophenyl)-2-tetrazolium, monosodium salt]) was added to each well, and the plates were returned to the incubator for 2 hours. The absorbance in each well of the plates was then measured using the Molecular Devices plate reader at 450 nm. Surviving fraction of cells at each concentration of taxoid or conjugate are plotted in FIGS. 2 *a,b*.

The results demonstrate that conjugation to antibodies renders high target specificity to the taxoid. Thus huC242-taxoid is very potent in killing target human colon cancer COLO 205 cells with an $IC_{50}$ value of $3.1 \times 10^{-10}$ M. In contrast, antigen negative cells are about 94-fold less sensitive, with an $IC_{50}$ value of $2.9 \times 10^{-8}$ M, demonstrating the antigen specificity of the cytotoxic effect (FIG. 2*a*). The free taxoid, on the other hand, is equally potent towards both cell lines ($IC_{50} \sim 8 \times 10^{-10}$ M (FIG. 2*b*).

What is claimed is:

1. A taxane compound having the following formula (I):

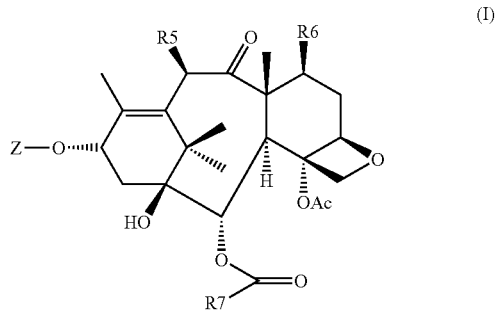

-continued (II)

wherein Z=H or a radical of formula II;
R₁ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR₂ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;
R₂ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;
R₃ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;
R₄ is an H or a linker, or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxy-carbonyl, alkenyloxycarbonyl, alkynyloxycarbonyl, optionally substituted aryl or heterocyclyl, aroyl or heterocyclylcarbonyl, aryloxycarbonyl or heterocyclyloxy-carbonyl or OR₄ forms a carbamate of the formula —OCOX, wherein X is a nitrogen-containing heterocycle, or a carbamate of the formula —OCONR₈R₉, wherein R₈ and R₉ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;
R₅ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR₅ forms a carbamate of the formula —OCOX, wherein X is a nitrogen-containing heterocycle, or a carbamate of the formula —OCONR₁₀R₁₁, wherein R₁₀ and R₁₁ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;
R₆ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR₆ forms a carbamate of the formula —OCOX, wherein X is a nitrogen-containing heterocycle, or a carbamate of the formula —OCONR₁₂R₁₃, wherein R₁₂ and R₁₃ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and
R₇ is an optionally substituted heterocyclic radical;
provided that one, and only one, of R₁, R₃, R₄, R₅, or R₆ is a linker.

2. A taxane compound having the following formula (I):

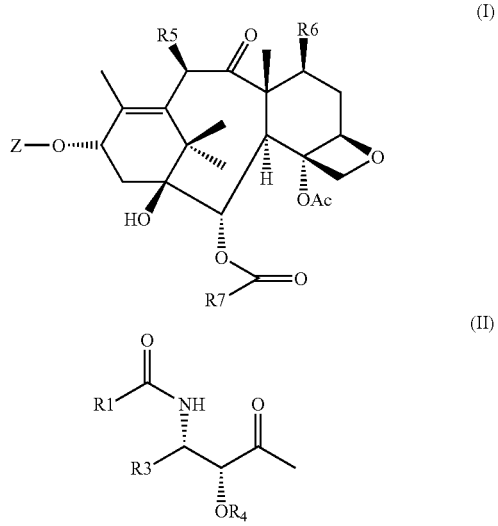

wherein Z=H or a radical of formula II;
R₁ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR₂ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;
R₂ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or a linker, or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxy-carbonyl, alkenyloxycarbonyl, alkynyloxycarbonyl, optionally substituted aryl or heterocyclyl, aroyl or heterocyclylcarbonyl, aryloxycarbonyl or heterocyclyloxy-carbonyl or $OR_4$ forms a carbamate of the formula —OCOX, wherein X is unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical;

provided that one, and only one, of $R_1$, $R_3$, $R_4$, $R_5$, or $R_6$ is a linker.

3. A compound according to claim 1 wherein $R_1$ is —OR$_2$ or an optionally substituted aryl or a heterocyclic radical.

4. A compound according to claim 1 wherein $R_2$ is an alkyl group.

5. A compound according to claim 1 wherein $R_2$ is a tert-butyl group.

6. A compound according to claim 1 wherein $R_5$ is a linker or H.

7. A compound according to claim 1 wherein $R_1$ is selected from the group consisting of t-butoxy, crotyl, dimethylacrylyl, isobutenyl, hexenyl, cyclopentenyl, cyclohexenyl, furyl, pyrrolyl, thienyl, thiazolyl, imidazolyl, pyridyl, morpholino, piperidino, piperazino, oxazolyl, indolyl, benzofuranyl and benzothienyl.

8. A compound according to claim 7 wherein $R_1$ is t-butoxy, isobutenyl, crotyl, dimethyacrylyl, thienyl, thiazolyl or furyl.

9. A compound according to claim 1 wherein $R_3$ is selected from the group consisting of crotyl, dimethylacrylyl, propenyl, isobutenyl, hexenyl, cyclopentenyl, cyclohexenyl, furyl, pyrrolyl, thienyl, thiazolyl, imidazolyl, pyridyl, oxazolyl, indolyl, benzofuranyl and benzothienyl.

10. A compound according to claim 9 wherein $R_3$ is isobutenyl, crotonyl, dimethylacrylyl, thienyl, thiazolyl, pyridyl, tert-butyl, or furyl.

11. A compound according to claim 1 wherein the linking groups independently contain groups selected from the group consisting of disulfide groups, thioether groups, acid labile groups, photolabile groups, peptidase labile groups and esterase labile groups.

12. A compound according to claim 11 wherein the linking groups independently contain groups selected from the group consisting of disulfide groups and thioether groups.

13. A compound according to claim 11 wherein the linking groups independently contain a thiol- or disulfide-containing group, and wherein the side chain carrying the thiol or disulfide group can be linear or branched, aromatic or heterocyclic.

14. A compound according to claim 11 wherein for $R_5$ and $R_6$ the linking group is selected from the group consisting of —O(CR$_{15}$R$_{16}$)$_m$(CR$_{17}$R$_{18}$)$_n$(OCH$_2$CH$_2$)$_y$SZ', —OCO(CR$_{15}$R$_{16}$)$_m$(CR$_{17}$R$_{18}$)$_n$(OCH$_2$CH$_2$)$_y$SZ', —O(CR$_{15}$R$_{16}$)$_m$(CR$_{19}$=CR$_{20}$)(CR$_{17}$R$_{18}$)$_m$(OCH$_2$CH$_2$)$_y$SZ', —OCO—(CR$_{15}$R$_{16}$)$_m$ (CR$_{19}$=CR$_{20}$)(CR$_{17}$R$_{18}$)$_m$(OCH$_2$CH$_2$)$_y$SZ', —OCONR$_{14}$(CR$_{15}$R$_{16}$)$_m$(CR$_{17}$R$_{18}$)$_n$(OCH$_2$CH$_2$)$_y$SZ', —OCO-phenyl-X'SZ', —OCO-furyl-X'SZ', —OCO-oxazolyl-X'SZ', —OCO-thiazolyl-X'SZ', —OCO-thienyl-X'SZ', —OCO-imidazolyl-X'SZ', —OCO-morpholino-X'SZ', —OCO-piperazino-X'SZ', —OCO-piperidino-X'SZ', and —OCO-N-methylpiperazino-X'SZ', or —OCO-N-methyl-piperazino-X'SZ', wherein:

Z' is H, SR', SCOR' or a thiol protective group;

and wherein —X' is a linear alkyl or branched alkyl having from 1-10 carbon atoms or a polyethylene glycol spacer with 2 to 20 repeating ethylene oxy units;

R' and $R_{14}$ are the same or different and are linear alkyl, branched alkyl or cyclic alkyl having from 1 to 10 carbon atoms, or unsubstituted or substituted aryl or heterocyclic, and $R_{14}$ can in addition be H;

—$R_{15}$, $R_{16}$, $R_{17}$ and $R_{18}$ are the same or different and are H or a linear or branched alkyl having from 1 to 4 carbon atoms;

—$R_{19}$ and $R_{20}$ are H or methyl;

n is an integer of 1 to 10;

m is an integer from 1 to 10 and can also be 0; and y is an integer from 1 to 20 and can also be 0.

15. A compound according to claim 11 wherein for $R_1$ the linking group is chosen from the group consisting of —$(CR_{15}R_{16})_m(CR_{17}R_{18})_n(OCH_2CH_2)_ySZ'$, —$O(CR_{15}R_{16})_m(CR_{17}R_{18})_n(OCH_2CH_2)_ySZ'$, —$(CR_{15}R_{16})_m(CR_{19}=CR_{20})(CR_{17}R_{18})_m(OCH_2CH_2)_ySZ'$, —$O$—$(CR_{15}R_{16})_m(CR_{19}=CR_{20})(CR_{17}R_{18})_m(OCH_2CH_2)_ySZ'$, —$NR_{14}(CR_{15}R_{16})_m(CR_{17}R_{18})_n(OCH_2CH_2)_ySZ'$, -phenyl-X'SZ', -furyl-X'SZ', -oxazolyl-X'SZ', thiazolyl-X'SZ', -thienyl-X'SZ', -imidazolyl-X'SZ', -morpholino-X'SZ', -piperazino-X'SZ', -piperidino-X'SZ', piperidino-X'SZ', —N-methylpiperazino-X'SZ', and —N-methylpiperazino-X'SZ', wherein:

Z' is H, SR', SCOR' or a thiol protective group;

wherein X' is a direct link or a linear alkyl or branched alkyl having from 1-10 carbon atoms or a polyethylene glycol spacer with 2 to 20 repeating ethylene oxy units;

R' and R14 are the same or different and are linear alkyl, branched alkyl or cyclic alkyl having from 1 to 10 carbon atoms, or unsubstituted or substituted aryl or heterocyclic, and $R_{14}$ can in addition be H;

$R_{15}$, $R_{16}$, $R_{17}$ and $R_{18}$ are the same or different and are H or a linear or branched alkyl having from 1 to 4 carbon atoms;

$R_{19}$ and $R_{20}$ are H or alkyl;

n is an integer of 1 to 10;

m is an integer from 1 to 10 and can also be 0; and y is an integer from 1 to 20 and can also be 0.

16. Compounds of claim 11 wherein for $R_4$ the linking group is selected from the group consisting of —$CO(CR_{15}R_{16})_m(CR_{17}R_{18})_n(OCH_2CH_2)_ySZ'$, —$CO$—$(CR_{15}R_{16})_m(CR_{19}=CR_{20})(CR_{17}R_{18})_m(OCH_2CH_2)_ySZ'$, —$CONR_{14}(CR_{15}R_{16})_m(CR_{17}R_{18})_n(OCH_2CH_2)_ySZ'$, CO-furyl-X'SZ', CO-thienyl-X'SZ', CO-thiazolyl-X'SZ', —CO—N-methylpiperazino-X'SZ', —CO-morpholino-X'SZ', —CO-piperazino-X'SZ', —CO-piperidino-X'SZ', and —CO—N-methylpiperazino-X'SZ', wherein:

Z' is H, SR', SCOR' or a thiol protective group;

X' is a linear alkyl or branched alkyl having from 1-10 carbon atoms or a polyethylene glycol spacer with 2 to 20 repeating ethylene oxy units;

R' and $R_{14}$ are the same or different and are linear alkyl, branched alkyl or cyclic alkyl having from 1 to 10 carbon atoms, or unsubstituted or substituted aryl or heterocyclic, and $R_{14}$ can in addition be H;

$R_{15}$, $R_{16}$, $R_{17}$ and $R_{18}$ are the same or different and are H or a linear or branched alkyl having from 1 to 4 carbon atoms;

$R_{19}$ and $R_{20}$ are H or methyl;

n is an integer of 1 to 10;

m is an integer from 1 to 10 and can also be 0; and y is an integer from 1 to 20 and can also be 0.

17. A compound according to claim 1 wherein $R_7$ is furyl, pyrrolyl, thienyl, thiazolyl, imidazolyl, pyridyl, indolyl, benzofuranyl or benzothienyl.

18. A compound according to claim 1 wherein in the compound of formula (I)

$R_5$ is a linker;

Z is H or a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —$OCONR_8R_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —$OCONR_{12}R_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

19. A compound according to claim 1 wherein in the compound of formula (I)

$R_5$ is a linker;

Z is H or a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

20. A compound according to claim 1 wherein:

$R_1$ is a linker;

Z is a radical of formula II;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

21. A compound according to claim 1 wherein:

$R_1$ is a linker;

Z is a radical of formula II;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxy-carbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

22. A compound according to claim 1 wherein:

$R_3$ is a linker;

Z is a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$, forms a carbamate of the formula —OCOX, wherein X is a nitrogen-containing heterocycle, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_2$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and R$_7$ is an optionally substituted heterocyclic radical.

23. A compound according to claim 1 wherein:

R$_3$ is a linker;

Z is a radical of formula II;

R$_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

R$_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

R$_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or OR$_4$ forms a carbamate of the formula —OCOX, wherein X is unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

R$_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR$_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

R$_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR$_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and R$_7$ is an optionally substituted heterocyclic radical.

24. A compound according to claim 1 wherein:

R$_4$ is a linker;

Z is a radical of formula II;

R$_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

R$_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

R$_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

R$_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR$_5$ forms a carbamate of the formula —OCOX, wherein X is a nitrogen-containing heterocycle, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_{12}$R$_{13}$, wherein R$_{12}$ and R13 are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

25. A compound according to claim 1 wherein:

$R_4$ is a linker;

Z is a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

26. A compound according to claim 1 wherein:

$R_6$ is a linker;

Z is H or a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, $OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

27. A compound according to claim 1 wherein:

$R_6$ is a linker;

Z is H or a radical of formula II;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or OR4 forms a carbamate of the formula —OCOX, wherein X is unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein R$_{10}$ and R$_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

28. A cytotoxic agent comprising one or more taxanes covalently bonded to a cell binding agent through a linking group, wherein at least one of said taxanes is a compound represented by formula (III):

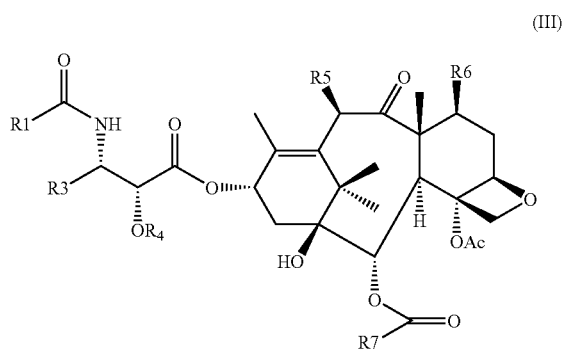

(III)

wherein:

$R_5$ is a linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or hetero cyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or OR$_4$ forms a carbamate of the formula —OCOX, wherein X is a nitrogen-containing heterocycle, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_{12}$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

29. A cytotoxic agent according to claim 21 comprising one or more taxanes covalently bonded to a cell binding agent through a linker, wherein at least one of said taxanes is a compound represented by formula (III):

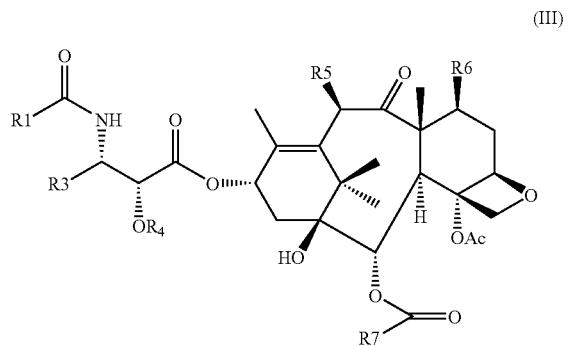

wherein:

$R_5$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is unsubstituted or substituted piperidino, morpholino, piperazino, N-methylpiperazino, or a carbamate of the formula —OCONR$_8$R$_9$, wherein R$_8$ and R$_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein R$_{12}$ and R$_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

30. A cytotoxic agent comprising one or more taxanes covalently bonded to a cell binding agent through a linker, wherein at least one of said taxanes is a compound represented by formula (III):

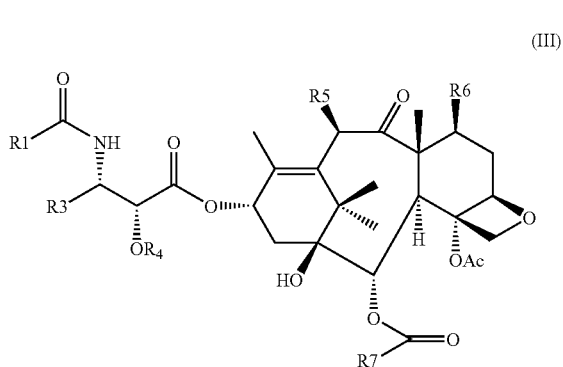

wherein:

$R_1$ is the linker;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —$OCONR_8R_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —$OCONR_{10}R_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —$OCONR_{12}R_{13}$, wherein $R_{12}$ and $R_{12}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

31. A cytotoxic agent according to claim 30 comprising one or more taxanes covalently bonded to a cell binding agent through a linker, wherein at least one of said taxanes is a compound represented by formula (III):

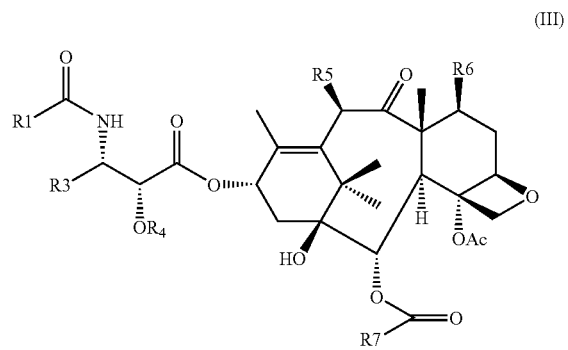

wherein:

$R_1$ is the linker;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is unsubstituted or substituted piperidino, morpholino, piperazino, N-methylpiperazino, or a carbamate of the formula —$OCONR_8R_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —$OCONR_{10}R_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

32. A cytotoxic agent comprising one or more taxanes covalently bonded to a cell binding agent through a linker, wherein at least one of said taxanes is a compound represented by formula (III):

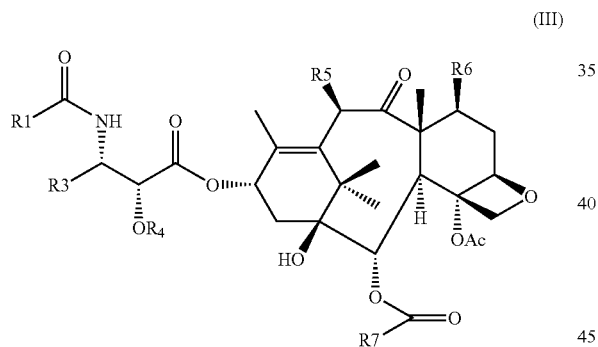

wherein:

$R_3$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

33. A cytotoxic agent according to claim 32 comprising one or more taxanes covalently bonded to a cell binding agent through a linker, wherein at least one of said taxanes is a compound represented by formula (III):

(III)

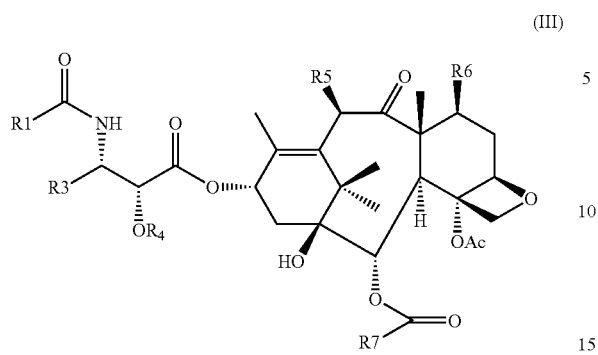

wherein:

$R_3$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or OR4 forms a carbamate of the formula —OCOX, wherein X is unsubstituted or substituted piperidino, morpholino, piperazino, N-methylpiperazino, or a carbamate of the formula —$OCONR_8R_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —$OCONR_{10}R_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —$OCONR_{12}R_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

34. A cytotoxic agent comprising one or more taxanes covalently bonded to a cell binding agent through a linker, wherein at least one of said taxanes is a compound represented by formula (III):

(III)

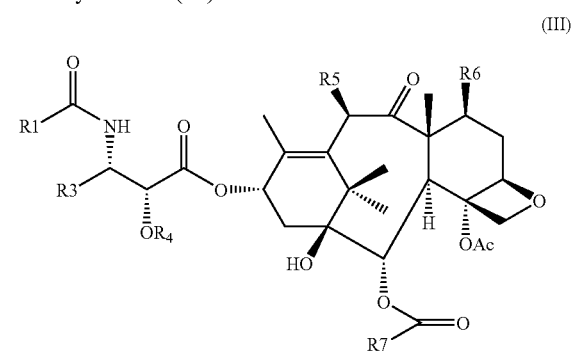

wherein:

$R_4$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is a nitrogen-containing heterocycle, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —OCONR$_{12}$R$_3$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

35. A cytotoxic agent according to claim 34 comprising one or more taxanes covalently bonded to a cell binding agent through a linker, wherein at least one of said taxanes is a compound represented by formula (III):

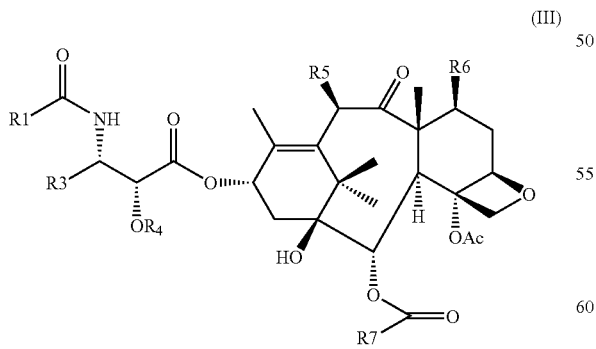

(III)

wherein:

$R_4$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ forms a carbamate of the formula —OCOX, wherein X is unsubstituted or substituted piperidino, morpholino, piperazino, N-methylpiperazino, or a carbamate of the formula —OCONR$_{10}$R$_{11}$, wherein $R_{10}$ and $R_{11}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_6$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

36. A cytotoxic agent comprising one or more taxanes covalently bonded to a cell binding agent through a linker, wherein at least one of said taxanes is a compound represented by formula (III):

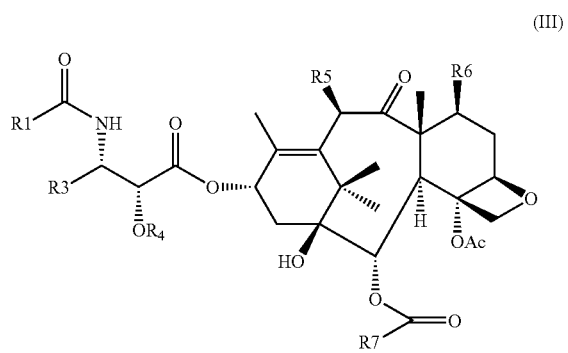

(III)

wherein:

$R_6$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxycarbonyl, optionally substituted aryl or heterocyclyl, aroyl or heterocyclylcarbonyl, aryloxycarbonyl or heterocyclyloxycarbonyl or $OR_4$ forms a carbamate of the formula —OCOX, wherein X is a nitrogen-containing heterocycle, or a carbamate of the formula —$OCONR_8R_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ $R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_6$ forms a carbamate of the formula —OCOX, wherein X is a nitrogen-containing heterocycle, or a carbamate of the formula —$OCONR_{12}R_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

37. A cytotoxic agent according to claim 36 comprising one or more taxanes covalently bonded to a cell binding agent through a linker, wherein at least one of said taxanes is a compound represented by formula (III):

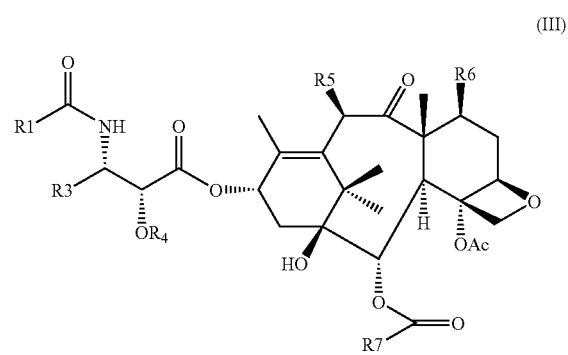

(III)

wherein:

$R_6$ is the linker;

$R_1$ is an optionally substituted aryl or heterocyclic radical, alkyl having from 1 to 10 carbon atoms, alkynyl or alkenyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkynyl or alkenyl having from 2 to 10 carbon atoms, cycloalkyl or cycloalkenyl having from 3 to 10 carbon atoms, or optionally substituted aryl or heterocyclyl radical;

$R_2$ is alkyl having from 1 to 10 carbon atoms, alkynyl or alkenyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is an H or an optionally substituted, linear, or branched alkyl radical having from 1 to 10 carbon atoms, alkenyl having from 2 to 10 carbon atoms, alkynyl having from 3 to 10 carbon atoms, cycloalkyl or cycloalkenyl having from 3 to 10 carbon atoms, alkanoyl, alkenoyl, alkynoyl, alkoxyacetyl, alkenyloxyacetyl, alkynyloxyacetyl, alkylthioacetyl, alkenylthioacetyl, alkynylthioacetyl, alkyloxycarbonyl, alkenyloxy-carbonyl, alkynyloxy-carbonyl, optionally substituted aryl or heterocyclyl, aroyl or heterocyclylcarbonyl, aryloxycarbonyl or heterocyclyloxycarbonyl $OR_4$ forms a carbamate of the formula —OCOX, wherein X is unsubstituted or substituted piperidino, morpholino, piperazino, N-methylpiperazino, or a carbamate of the formula —OCONR$_8$R$_9$, wherein $R_8$ and $R_9$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl;

$R_5$ is H or hydroxyl or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or $OR_5$ $R_6$ is H or hydroxyl or a linker, or an optionally substituted, linear, or branched alkyloxy radical having from 1 to 10 carbon atoms, alkenyloxy having from 2 to 10 carbon atoms, alkynyloxy having from 3 to 10 carbon atoms, cycloalkyloxy or cycloalkenyloxy having from 3 to 10 carbon atoms, alkanoyloxy, alkenoyloxy, alkynoyloxy, alkoxyacetoxy, alkenyloxyacetoxy, alkynyloxyacetoxy, alkylthioacetoxy, alkenylthioacetoxy, alkynylthioacetoxy, alkyloxycarbonyloxy, alkenyloxycarbonyloxy, alkynyloxycarbonyloxy, optionally substituted aryloxy or heterocyclyloxy, aroyloxy or heterocyclylcarbonyloxy, aryloxycarbonyloxy or heterocyclyloxycarbonyloxy or OR6 forms a carbamate of the formula —OCOX, wherein X is unsubstituted or substituted piperidino, morpholino, piperazino, N-methylpiperazino, or a carbamate of the formula —OCONR$_{12}$R$_{13}$, wherein $R_{12}$ and $R_{13}$ are the same or different and are H, linear, branched, or cyclic alkyl having from 1 to 10 atoms, alkenyl having from 2 to 10 carbon atoms, alkynyl having from 3 to 10 carbon atoms, cycloalkyl or cycloalkenyl having from 3 to 10 carbon atoms, optionally substituted aryl, or optionally substituted heterocyclyl; and $R_7$ is an optionally substituted heterocyclic radical.

38. A therapeutic composition comprising:
a therapeutically effective amount of the cytotoxic agent according to any one of claims 28, 30, 32, 34, or 36; and
a pharmaceutically acceptable carrier.

39. The cytotoxic agent of any one of claims 28, 30, 32, 34, or 36 wherein the cell binding agent is selected from the group consisting of antibodies, an antibody fragment, interferons, lymphokines, hormones, vitamins, growth factors, colony stimulating factors, and transferrin.

40. The cytotoxic agent of any one of claims 28, 30, 32, 34, or 36 wherein the cell binding agent is an antibody.

41. The cytotoxic agent of any one of claims 28, 30, 32, 34, or 36 wherein the cell binding agent is a monoclonal antibody.

42. The cytotoxic agent of any one of claims 28, 30, 32, 34, or 36 wherein the cell binding agent is an antigen specific antibody fragment.

43. The cytotoxic agent of any one of claims 28, 30, 32, 34, or 36 wherein the antibody fragment is sFV, Fab, Fab', or F(ab')2.

44. The cytotoxic agent of any one of claims 28, 30, 32, 34, or 36 wherein the cell binding agent is a growth factor or colony stimulating factor.

45. A method of killing selected cell populations comprising contacting target cells or tissue containing target cells with an effective amount of the cytotoxic agent of any one of claims 28, 30, 32, 34, or 36.

* * * * *

UNITED STATES PATENT AND TRADEMARK OFFICE
CERTIFICATE OF CORRECTION

PATENT NO. : 7,598,290 B2 Page 1 of 1
APPLICATION NO. : 11/679347
DATED : October 6, 2009
INVENTOR(S) : Michael L. Miller, Ravi V. J. Chari and Erkan Baloglu It is certified that error appears in the above-identified patent and that said Letters Patent is hereby corrected as shown below:

Column 65, line 28, please replace the dependency of claim 29 to read:

claim ~~21~~ 28

Column 76, line 2 should read:

loxy or OR$_5$ ~~R$_6$~~ is H or hydroxyl or a linker, or an

Column 76, line 14 should read:

or heterocyclyloxycarbonyloxy or ~~OR$_6$~~ OR$_5$ forms a carbam-

Signed and Sealed this

Thirteenth Day of April, 2010

David J. Kappos
*Director of the United States Patent and Trademark Office*